US012053350B2

(12) United States Patent
Salah et al.

(10) Patent No.: US 12,053,350 B2
(45) Date of Patent: Aug. 6, 2024

(54) METHOD FOR ANALYZING AN IMAGE OF A DENTAL ARCH

(71) Applicant: DENTAL MONITORING, Paris (FR)

(72) Inventors: Philippe Salah, Paris (FR); Thomas Pellissard, Paris (FR); Guillaume Ghyselinck, Cantin (FR); Laurent Debraux, Paris (FR)

(73) Assignee: DENTAL MONITORING, Paris (FR)

( * ) Notice: Subject to any disclaimer, the term of this patent is extended or adjusted under 35 U.S.C. 154(b) by 0 days.

(21) Appl. No.: 18/371,950

(22) Filed: Sep. 22, 2023

(65) Prior Publication Data

US 2024/0008962 A1    Jan. 11, 2024

Related U.S. Application Data

(63) Continuation of application No. 17/327,541, filed on May 21, 2021, which is a continuation-in-part of (Continued)

(30) Foreign Application Priority Data

Jul. 21, 2017    (FR) ...................................... 1756956

(51) Int. Cl.
*G06K 9/00* (2022.01)
*A61C 7/00* (2006.01)
(Continued)

(52) U.S. Cl.
CPC ............ *A61C 9/0046* (2013.01); *A61C 7/002* (2013.01); *A61C 7/08* (2013.01); *A61C 7/14* (2013.01);
(Continued)

(58) Field of Classification Search
CPC ............... A61C 7/00; A61C 7/18; G06K 9/00
(Continued)

(56) References Cited

U.S. PATENT DOCUMENTS 7,912,257 B2    3/2011  Paley et al.
9,014,440 B2    4/2015  Arumugam et al.
(Continued)

FOREIGN PATENT DOCUMENTS

EP    3496592 A    6/2019
JP    4576325 A    6/2007
(Continued)

OTHER PUBLICATIONS

*Dental Monitoring v. Get-Grin Inc.*, C.A. No. 22-647 (WCB) (Consolidated), Defendant Get-Grin Inc.'s Invalidity Contentions, Sep. 25, 2023.
(Continued)

*Primary Examiner* — Seyed H Azarian
(74) *Attorney, Agent, or Firm* — Ronald M. Kachmarik; Cooper Legal Group LLC

(57) ABSTRACT

A method and associated system. Such is for orthodontic treatment or for assessing shape of an aligner. Within an example, there is participation in communication of an assessment of the suitability of an aligner as a function of the value of: a tooth attribute of an analysis tooth zone of an analysis image, the tooth attribute relating to a separation between the tooth represented by the analysis tooth zone and the aligner represented on the analysis image, or an image attribute of an analysis image, the image attribute relating to a separation between at least one tooth represented on the analysis image and the aligner represented on the analysis image. The analysis image is an image of an aligner in a
(Continued)

service position in which it is worn by the patient acquired by a cellphone more than 1 week, and is a photograph, or an image extracted from a film.

14 Claims, 13 Drawing Sheets

Related U.S. Application Data application No. 16/030,137, filed on Jul. 9, 2018, now Pat. No. 11,049,248.

(51) Int. Cl.

| | |
|---|---|
| A61C 7/08 | (2006.01) |
| A61C 7/14 | (2006.01) |
| A61C 7/18 | (2006.01) |
| A61C 7/36 | (2006.01) |
| A61C 9/00 | (2006.01) |
| G06N 3/04 | (2023.01) |
| G06N 3/08 | (2023.01) |
| G06T 7/00 | (2017.01) |
| G06T 7/11 | (2017.01) |
| G06T 7/149 | (2017.01) |
| G06T 7/60 | (2017.01) |
| G06V 10/82 | (2022.01) |
| G16H 10/60 | (2018.01) |
| G16H 30/40 | (2018.01) |

(52) U.S. Cl.
CPC ............... *A61C 7/36* (2013.01); *A61C 9/004* (2013.01); *G06N 3/04* (2013.01); *G06N 3/08* (2013.01); *G06T 7/0016* (2013.01); *G06T 7/11* (2017.01); *G06T 7/149* (2017.01); *G06T 7/60* (2013.01); *G06V 10/82* (2022.01); *G16H 10/60* (2018.01); *G16H 30/40* (2018.01); *G06T 2207/20081* (2013.01); *G06T 2207/20084* (2013.01); *G06T 2207/30036* (2013.01)

(58) Field of Classification Search
USPC ........ 382/100, 103, 106, 128–131, 154–155, 382/162, 168, 173, 181, 199, 219, 224, 382/232, 254, 285–291, 305, 312; 433/2, 433/3, 24
See application file for complete search history.

(56) References Cited

U.S. PATENT DOCUMENTS

| | | | |
|---|---|---|---|
| 9,152,767 | B2 | 10/2015 | Mah |
| 9,770,217 | B2 | 9/2017 | Sandholm et al. |
| 10,032,271 | B2 | 7/2018 | Somasundaram et al. |
| 10,136,972 | B2 | 11/2018 | Sabina et al. |
| 10,242,443 | B2 | 3/2019 | Hsieh et al. |
| 10,463,451 | B2 | 11/2019 | Janzadeh et al. |
| 10,467,815 | B2 | 11/2019 | Marom et al. |
| 10,504,386 | B2 | 12/2019 | Levin et al. |
| 10,588,723 | B2 | 3/2020 | Falkel |
| 10,660,728 | B2 | 5/2020 | Maraj et al. |
| 10,755,409 | B2 | 8/2020 | Salah et al. |
| 10,779,718 | B2 | 9/2020 | Meyer et al. |
| 11,049,248 | B2 | 6/2021 | Salah et al. |
| 11,109,945 | B2 | 9/2021 | Salah et al. |
| 11,291,532 | B2 | 4/2022 | Glidewell |
| 11,314,983 | B2 | 4/2022 | Salah et al. |
| 11,532,079 | B2 | 12/2022 | Salah et al. |
| 11,599,997 | B2 | 3/2023 | Salah et al. |
| 11,638,636 | B2 | 5/2023 | Oren-Artzi et al. |
| 2013/0230818 | A1* | 9/2013 | Matov ...................... A61C 7/16 433/3 |
| 2013/0244197 | A1 | 9/2013 | Tjioe et al. |
| 2013/0282351 | A1 | 10/2013 | Tank |
| 2015/0132708 | A1* | 5/2015 | Kuo .......................... A61C 7/08 433/2 |
| 2016/0310097 | A1* | 10/2016 | Bae .......................... A61B 6/51 |
| 2016/0374784 | A1 | 12/2016 | Joshi |
| 2017/0049311 | A1* | 2/2017 | Borovinskih ........... G06T 7/136 |
| 2017/0258420 | A1 | 9/2017 | Inglese et al. |
| 2017/0281313 | A1 | 10/2017 | Kim |
| 2017/0300207 | A1* | 10/2017 | Wen ...................... G06F 3/0484 |
| 2017/0337682 | A1 | 11/2017 | Liao et al. |
| 2018/0110590 | A1 | 4/2018 | Maraj et al. |
| 2018/0125610 | A1 | 5/2018 | Carrier, Jr. et al. |
| 2018/0168780 | A1* | 6/2018 | Kopelman ............. A61C 1/082 |
| 2018/0228359 | A1 | 8/2018 | Meyer et al. |
| 2019/0026893 | A1 | 1/2019 | Salah et al. |
| 2019/0167115 | A1 | 6/2019 | Dorodvand et al. |
| 2020/0229901 | A1 | 7/2020 | Carrier, Jr. et al. |
| 2021/0068923 | A1 | 3/2021 | Carrier, Jr. et al. |
| 2021/0282634 | A1 | 9/2021 | Oren-Artzi et al. |

FOREIGN PATENT DOCUMENTS

| | | |
|---|---|---|
| JP | 2017031794 A | 2/2017 |
| JP | 2018134418 A | 8/2018 |
| KR | 101583547 B1 | 1/2016 |
| WO | 2016066651 A1 | 5/2016 |
| WO | 2018029276 A1 | 2/2018 |
| WO | 2018/069736 A1 | 4/2018 |
| WO | 2018155630 A1 | 8/2018 |

OTHER PUBLICATIONS

Kevis-Kokitsi Maninis, et al., "Convolutional Oriented Boundaries: From Image Segmentation to High-Level Tasks", Arxiv.org (Cornell University), Apr. 28, 2017, 14 pages.

Kevis-Kokitsi Maninis, et al., "Convolutional Oriented Boundaries: From Image Segmentation to High-Level Tasks", Arxiv.org (Cornell University), Jan. 17, 2017, 14 pages.

Maurice Carrier, et al., "Methods and Apparatuses for Dental Images", Provisional Prosecution History, U.S. Appl. No. 62/417,985, filed Nov. 4, 2016, 66 pages.

Eric P. Meyer, et al., "Cheek Retractor and Mobile Device Holder", Provisional Prosecution History, U.S. Appl. No. 62/458,477, filed Feb. 13, 2017, 55 pages.

*Dental Monitoring SAS v. Align Technology, Inc.*, Case. No. 3:22-cv-7335-WHA, Defendant Align Technology, Inc's Motion for Summary Judgement Pursuant to the Court's Patent Showdown Procedure, Jan. 4, 2024.

"Invisalign Clinical Monitoring Guide", Align Technology, Inc., Aug. 8, 2003, 52 pages.

*Dental Monitoring SAS v. Align Technology, Inc.*, Case. No. 3:22-cv-7335-WHA, Defendant's Patent Local Rule 3-3 and 3-4 Initial Invalidity Contentions and Disclosures, Sep. 11, 2023.

Scott Frey, "DIY Dental Monitoring Solution", The Ortho Cosmos, Apr. 29, 2017, 12 pages.

*Dental Monitoring SAS v. Align Technology, Inc.*, Case. No. 3:22-cv-7335-WHA, Opening Brief in Support of Motion for Summary Judgment of Infringement, Jan. 4, 2024.

*Dental Monitoring SAS v. Align Technology, Inc.*, Case. No. 3:22-cv-7335-WHA, Brief in Opposition to Defendant's Motion for Summary Judgement, Jan. 2, 2024.

*Dental Monitoring SAS v. Align Technology, Inc.*, Case. No. 3:22-cv-7335-WHA, Align's Opposition to Dental Monitoring's Motion for Summary Judgment Pursuant to the Court's Patent Showdown Procedure, Feb. 1, 2024.

*Dental Monitoring SAS v. Align Technology, Inc.*, Case. No. 3:22-cv-7335-WHA, Align's Reply in Support of Its Motion for Summary Judgment Pursuant to the Court's Patent Showdown Procedure, Feb. 15, 2024.

*Align Technology, Inc. v. Dental Monitoring SAS*, Case No. IPR2023-01369, Petition for Inter Partes Review of U.S. Pat. No. 10,755,409, Aug. 31, 2023.

(56) References Cited

OTHER PUBLICATIONS

*Align Technology, Inc.* v. *Dental Monitoring SAS*, Case No. IPR2023-01369, Patent Owner's Preliminary Response, Dec. 7, 2023.
*Align Technology, Inc.* v. *Dental Monitoring SAS*, Case No. IPR2024-00110, Petition for Inter Partes Review of U.S. Pat. No. 11,109,945, Oct. 31, 2023.
*Dental Monitoring SAS* v. *Align Technology, Inc.*, Case. No. 3:22-cv-7335-WHA, Dental Monitoring SAS's Reply Brief in Support of Its Motion for Summary Judgment of Infringement, Feb. 15, 2024.
*Align Technology, Inc.* v. *Dental Monitoring SAS*, Case No. IPR2024-00052, Petition for Inter Partes Review of U.S. Pat. No. 11,049,248, Oct. 16, 2023.
*Align Technology, Inc.* v. *Dental Monitoring SAS*, Case No. IPR2024-00052, Patent Owner's Preliminary Response, Jan. 30, 2024.
Philippe Salah, "DM GoLive—The World's First Dynamic Aligner Tracking System", Indeed, May 10, 2017.
Align Technology, Inc., "Instructions for Use", MKT-0007526, Revision E, Automated Notifications Available with Invisalign Virtual Care AI Version 3.0, Aug. 2022.
Align Technology, Inc., "MyInvisalign Mobile Application Terms of Use", Nov. 4, 2022.
Align Technology, Inc., "Invisalign Virtual Care AI, Practice Implementation Guide", 2023.
Align Technology, Inc., "Align Technology's Next Generation Invisalign Virtual Care AI-Assisted Remote Monitoring Solution Automates and Streamlines Practice Workflows", Press Release, Sep. 28, 2022, https://investor.aligntech.com/news-releases/news-release-details/align-technologys-next-generation-invisalign-virtual-care-ai.
Align Technology, Inc., "Align Technology Introduces Virtual Solutions To Connect Doctors and Existing Invisalign Patients for Continuity of Care", Press Release, May 7, 2020, https://investor.aligntech.com/news-releases/news-release-details/align-technology-introduces-virtual-solutions-connect-doctors.
Align Technology, Inc., "Invisalign Virtual Care AI, APAC Practice Implementation Guide", 2023.
François Chollet, "Deep Learning with Python", Dec. 22, 2017, pp. 5 and 94.
Align Technology, Inc., "Align Technology Wins "Best Virtual Care Platform" Award From Medtech Breakthrough", Press Release, May 6, 2021, https://investor.aligntech.com/news-releases/news-release-details/align-technology-wins-best-virtual-care-platform-award-medtech.
Yann LeCun, et al., "Deep Learning", Nature, vol. 521, May 2015, pp. 436-444.
Alvin Rajkomar, et al., "High-Throughput Classification of Radiographs Using Deep Convolutional Neural Networks", J Digit Imaging, Oct. 11, 2016. pp. 95-101.
Teny Handhayani, et al., "Comparison of Shallow and Deep Learning Models for Classification of Lasem Batik Patterns", Faculty of Information Technology, Tarumanagara University, Nov. 2017.
Alexios Koutsoukas, et al., "Deep-learning: investigating deep neural networks hyper-parameters and comparison of performance to shallow methods for modeling bioactivity data", Journal of Cheminformatics, 2017.
Renzo Andri, et al., "YodaNN: An Architecture for Ultra-Low Power Binary-Weight CNN Acceleration", Department of Electrical, Electronic and Information Engineering, University of Bologna, Feb. 24, 2017.
Ashish Shrestha, "Deep Learning-Based Real-Time Auto Classification of Smartphone Measured Bridge Vibration Data", Sensors, 2020.
Rui Zhao, et al., "Changing clear aligners every 10 days or 14 days ? A randomised controlled trial", Australasian Orthodontic Journal vol. 39, No. 1, 2023.
Jialing Liu, et al., "Machine learning in orthodontics: Challenges and perspectives", Advances in Clinical and Experimental Medicine, 2021.
Timothy Wheeler, "Orthodontic clear aligner treatment", Seminars in Orthodontics, vol. 23, No. 1, 2017, pp. 83-89.

Emilia Taneva, et al., "3D Scanning, Imaging, and Printing in Orthodontics", Intech, 2015, pp. 147-188.
Orhan Tuncay, et al., "Effectiveness of a Compliance Indicator for Clear Aligners", JCO, Inc., vol. XLIII, No. 4, 2009, pp. 263-268.
Silvia Caruso, et al., "A Knowledge-Based Algorithm for Automatic Monitoring of Orthodontic Treatment: The Dental Monitoring System. Two Cases", Sensors, 2021.
Alex Krizhevsky, "ImageNet Classification with Deep Convolutional Neural Networks", Advances in Neural Informational Processing Systems, 2012.
Patrick Cavanagh, "Vision Research", Elsevier Ltd., 2011, pp. 1538-1551.
Mukta Prasad, et al., "Learning Class-specific Edges for Object Detection and Segmentation", Computer Vision, Graphics and Image Processing: 5th Indian Conference, ICVGIP, 2006.
Jun Xie, et al., "Semantic Instance Annotation of Street Scenes by 3D to 2D Label Transfer, "2016 IEEE Conference on Computer Vision and Pattern Recognition, 2016.
Liang-Chieh Chen, et al., "Beat the MTurkers: Automatic Image Labeling from Weak 3D Supervision", 2014 IEEE Conference on Computer Vision and Pattern Recognition, 2014.
Chong Wang, et al., "Simultaneous Image Classification and Annotation", CVPR 1, No. 2, 2009.
A. Criminisi, et al., "Single View Metrology", International Journal of Computer Vision (40)2, 2000.
Barry J. Glaser, "The Insider's Guide to Invisalign Treatment", 3L Publishing, 2017.
Nathan Silberman, et al., "NYU Depth Dataset V2", https://web.archive.org/web/20170705142032/https://cs.nyu.edu/~silberman/datasets/nyu_depth_v2.html, 2017.
The Pascal VOC 2012 Segmentation dataset, https://web.archive.org/web/20170713000522/http://host.robots.ox.ac.uk/pascal/VOC/voc2012/#data, 2017.
Karim Armanious, et al., "MedGAN: Medical Image Translation using GANs", XP055573262, Jun. 17, 2018.
Kelwin Fernandez, et al., "Teeth/Palate and Interdental Segmentation Using Artificial Neural Networks", International Conference on Computer Analysis of Images and Patterns, CAIP 2017; Sep. 17, 2012.
Anonymous, "Artificial Neural Network", Wikipedia, Jul. 5, 2018.
European Office Action from Corresponding European Application No. 19736741.0, dated Nov. 16, 2023.
The Berkeley Segementation Data Set (BSDS 500), https://web.archive.org/web/20160722194737/http://www.eecs.berkeley.edu/Research/Projects/CS/vision/grouping/resources.html, 2016.
The Pascal Voc 2010, https://web.archive.org/web/20170707024736/http://host.robots.ox.ac.uk/pascal/VOC/voc2010/#data, 2017.
The PASCAL-Context Dataset, https://web.archive.org/web/20170613074321/https://cs.stanford.edu/~roozbeh/pascal-context/, 2017.
*Dental Monitoring SAS* v. *Align Technology, Inc.*, Case. No. C 22-07335 WHA, Patent Showdown Scheduling Order, Jul. 14, 2023.
*Dental Monitoring SAS* v. *Align Technology, Inc.*, Case. No. C 22-07335 WHA, Order re Updated Patent Showdown Deadlines, Oct. 26, 2023.
*Dental Monitoring SAS* v. *Align Technology, Inc.*, Case. No. 3:22-cv-7335-WHA, Defendant's Align Technology Inc's Notice of Pending Inter Partes Review Petition, Dec. 18, 2023.
*Dental Monitoring SAS* v. *Align Technology, Inc.*, Case. No. C 22-07335 WHA, Order Denying Second Motion to Dismiss, Jul. 19, 2023.
Curriculum Vitae of Budi Kusnoto, D.D.S., M.S.
Declaration of Budi Kusnoto, D.D.S., M.S., dated Jan. 30, 2024.
Curriculum Vitae of John T. Mongan, M.D., Ph. D.
Declaration of John T. Mongan, M.D., Ph.D., dated Jan. 30, 2024.
Declaration of Joshua A. Krevitt In Support of Patent Owner's Motion for PRO HAC VICE Admission, IPR2023-01369, U.S. Pat. No. 10,755,409, dated Nov. 6, 2023.
Declaration of Joshua A. Krevitt In Support of Patent Owner's Motion for PRO HAC VICE Admission, IPR2024-00052, U.S. Pat. No. 10,049,248, dated Nov. 7, 2023.
Declaration of Dr. Hassan Foroosh, Case, No. IPR2024-00052, U.S. Pat. No. 11,049,248, dated Oct. 16, 2023.

(56) References Cited

OTHER PUBLICATIONS

Curriculum Vitae of Hassan Foroosh, Ph.D.
U.S. Appl. No. 16/030,137 File History.
Scott Frey, Blog—The Ortho Cosmos, (archived May 4, 2017 at http://web.archive.org/web/20170504155213/http://theorthocosmos.com:80/blog).
Declaration of Nathaniel E. Frank-Wright, dated Sep. 14, 2023.
Declaration of Mitra Derakhshan, dated Oct. 13, 2023.
United States District Courts—National Judicial Caseload Profile, available at https://www.uscourts.gov/sites/default/files/data_tables/fcms_na_distprofile0331.2023.pdf (Mar. 2023).
ArXiv.org Submission Help Page, https://arxiv.org/help/submit (as archived May 3, 2017, at https://web.archive.org/web/20170503071322/https://arxiv.org/help/submit).
ArXiv.org Article Replacement Help Page, https://arxiv.org/help/replace (as archived Jul. 18, 2017, at https://web.archive.org/web/20170718173822/https://arxiv.org/help/replace).
COB—Convolutional Oriented Boundaries, http://people.ee.ethz.ch/~cvlsegmentation/cob/ (as archived May 3, 2017, at http://web.archive.org/web/20170503233424/http://people.ee.ethz.ch/~cvlsegmentation/cob/).
ArXiv.org Author Search Page for Luc van Gool, https://arxiv.org/find/cs/1/au:+Gool_L/0/1/0/all/0/1 (as archived Jul. 8, 2017, at https://web.archive.org/web/20170708002617/https://arxiv.org/find/cs/1/au:+Gool_L/0/1/0/all/0/1).
ArXiv.org Article Replacement Help Page, https://arxiv.org/help/replace (as archived Sep. 8, 2016, at https://web.archive.org/web/20160908205209/https://arxiv.org/help/replace).
*Dental Monitoring SAS* v. *Align Technology, Inc.*, Case No. 3-22-cv-07335-WHA, Joint Stipulation and Proposed Order Aug. 30, 2023.

\* cited by examiner

METHOD FOR ANALYZING AN IMAGE OF A DENTAL ARCH

TECHNICAL FIELD

The present invention relates to the field of dental arch image analysis.

STATE OF THE ART

The most recent orthodontic treatments use images to assess the therapeutic situations. This assessment is conventionally performed by an orthodontist, which requires the patient to transmit these images to the orthodontist, even to make an appointment.

There is an ongoing need for a method simplifying the analysis of the images of dental arches of patients.

One aim of the invention is to address this need.

SUMMARY OF THE INVENTION

The invention proposes a method for analyzing an image, called "analysis image", of a dental arch of a patient, a method in which the analysis image is submitted to a deep learning device, preferably a neural network, in order to determine at least one value of a tooth attribute relating to a tooth represented on the analysis image, and/or at least one value of an image attribute relating to the analysis image.

Analysis by Tooth

The invention proposes in particular a method for detailed analysis of an image called "analysis image" of a dental arch of a patient, said method comprising the following steps:

1) creation of a learning base comprising more than 1000 images of dental arches, or "historical images", each historical image comprising one or more zones each representing a tooth, or "historical tooth zones", to each of which, for at least one tooth attribute, a tooth attribute value is assigned;
2) training of at least one deep learning device, preferably a neural network, by means of the learning base;
3) submission of the analysis image to said at least one deep learning device for it to determine at least one probability relating to an attribute value of at least one tooth represented on a zone representing, at least partially, said tooth in the analysis image, or "analysis tooth zone";
4) determination, as a function of said probability, of the presence of a tooth of said arch at a position represented by said analysis tooth zone, and of the attribute value of said tooth.

A first deep learning device, preferably a neural network, may in particular be implemented to assess a probability relating to the presence, at a location of said analysis image, of an analysis tooth zone.

A second deep learning device, preferably a neural network, may in particular be implemented to assess a probability relating to the type of tooth represented in an analysis tooth zone.

As will be seen in more detail hereinafter in the description, a detailed analysis method according to the invention advantageously makes it possible to immediately recognize the content of the analysis image.

The analysis image may advantageously be classified automatically. It may also be used immediately by a computer program.

The invention relies on the use of a deep learning device, preferably a neural network, the performance of which is directly linked to the richness of the learning base. There is therefore also a need for a method that makes it possible to rapidly enrich the learning base.

The invention therefore relates also to a method for enriching a learning base, notably intended for the implementation of a detailed analysis method according to the invention, said enrichment method comprising the following steps:

A) at an "updated" instant, production of a model of a dental arch of a patient, or "updated reference model", and segmentation of the updated reference model so as to produce, for each tooth, a "tooth model", and, for at least one tooth attribute, assignment of a tooth attribute value to each tooth model;
B) preferably less than 6 months, preferably less than 2 months, preferably less than 1 month, preferably less than a fortnight, preferably less than 1 week, preferably less than 1 day before or after the updated instant, preferably substantially at the updated instant, acquisition of at least one, preferably at least three, preferably at least ten, preferably at least one hundred images of said arch, or "updated images" in respective real acquisition conditions;
C) for each updated image, search for virtual acquisition conditions suitable for an acquisition of an image of the updated reference model, called "reference image", exhibiting a maximum match with the updated image in said virtual acquisition conditions, and acquisition of said reference image;
D) identification, in the reference image, of at least one zone representing a tooth model, or "reference tooth zone", and, by comparison of the updated image and of the reference image, determination, in the updated image, of a zone representing said tooth model, or "updated tooth zone";
E) assignment, to said updated tooth zone, of the tooth attribute value or values of said tooth model;
F) addition of the updated image enriched with a description of said updated tooth zone and its tooth attribute value or values, or "historical image", in the learning base.

In particular, each execution of the method described in WO 2016/066651 preferably generates more than three, more than ten, preferably more than one hundred updated images which, by an automated processing by means of the updated reference model, may produce as many historical images.

In a particular embodiment, the method for enriching a learning base comprises, in place of the steps A) to C), the following steps:

A') at an initial instant, production of a model of a dental arch of a patient, or "initial reference model", and segmentation of the initial reference model so as to produce, for each tooth, a "tooth model", and, for at least one tooth attribute, assignment of a tooth attribute value to each tooth model;
B') at an updated instant, for example spaced apart by more than a fortnight, preferably more than a month, even more than two months from the initial instant, acquisition of at least one, preferably at least three, preferably at least ten, preferably at least one hundred images of said arch, or "updated images", in respective real acquisition conditions;
C') for each updated image, search, by deformation of the initial reference model, for an updated reference model and virtual acquisition conditions suitable for an acquisition of an image of the updated reference model, called "reference image", exhibiting a maximum match with the updated image in said virtual acquisition conditions.

This method advantageously makes it possible, after generation of the initial reference model, preferably by means of a scanner, to enrich the learning base at different updated instants, without it being necessary to perform a new scan, and therefore without the patient having to go to the orthodontist. He or she may in fact acquire the updated images him or herself, as described in WO 2016/066651.

A single orthodontic treatment may thus lead to the production of hundreds of historical images.

The invention relates also to a method for training a deep learning device, preferably a neural network, comprising an enrichment of a learning base according to the invention, then the use of said learning base to train the deep learning device.

Global Analysis

The detailed analysis method described above advantageously allows for a fine analysis of the analysis image, the situation of each being preferably assessed.

Alternatively, the deep learning device may be used globally, the learning base containing historical images whose description provides a global attribute value for the image. In other words, the value of the image attribute relates to the whole image and not to part of the image. The attribute is not then a "tooth" attribute, but is an "image" attribute. For example, this image attribute may define whether, in light of the image as a whole or of a part of the image, the dental situation "is pathological" or "is not pathological", without each tooth being examined. The image attribute also makes it possible to detect, for example, whether the mouth is open or closed, or, more generally, whether the image is suitable for a subsequent treatment, for example whether it makes it possible to monitor the occlusion.

The image attribute may in particular relate to
- a position and/or an orientation and/or a calibration of an acquisition apparatus used to acquire said analysis image, and/or
- a quality of the analysis image, and in particular relating to the brightness, to the contrast or to the sharpness of the analysis image, and/or
- the content of the analysis image, for example to the representation of the arches, of the tongue, of the mouth, of the lips, of the jaws, of the gums, of one or more teeth or of a dental, preferably orthodontic, appliance.

When the image attribute refers to the content of the image, the description of the historical images of the learning base specifies a characteristic of this content. For example, it may specify the position of the tongue (for example "retracted") or the opening of the mouth of the patient (for example mouth open or closed) or the presence of a representation of a dental, preferably orthodontic, appliance and/or of its condition (for example appliance intact, broken or damaged).

A tooth attribute value may be used to define a value for an image attribute. For example, if a value of a tooth attribute is "tooth decayed", the value of an image attribute may be "unsatisfactory dental situation".

The image attribute may in particular relate to a therapeutic situation.

The invention proposes a method for global analysis of an analysis image of a dental arch of a patient, said method comprising the following steps:

1') creation of a learning base comprising more than 1000 images of dental arches, or "historical images", each historical image comprising an attribute value for at least one image attribute, or "image attribute value";

2') training of at least one deep learning device, preferably a neural network, by means of the learning base;

3') submission of the analysis image to the deep learning device for it to determine, for said analysis image, at least one probability relating to said image attribute value, and determination, as a function of said probability, of a value for said image attribute for the analysis image.

The image attribute may in particular relate to the orientation of the acquisition apparatus upon the acquisition of the analysis image. It may for example take the values "front photo", "left photo" and "right photo".

The image attribute may also relate to the quality of the image. It may for example take the values "insufficient contrast" and "acceptable contrast".

The image attribute may also relate to the dental situation of the patient, for example relate to the presence of decay or to the condition of a dental, preferably orthodontic, appliance worn by the patient ("degraded" or "in good condition" for example) or to the suitability of the dental, preferably orthodontic, appliance to the treatment of the patient (for example "unsuitable" or "suitable").

The image attribute may also relate to the "presence" or "absence" of a dental, preferably orthodontic, appliance, or to the state of opening of the mouth ("mouth open", "mouth closed" for example).

As will be seen in more detail hereinafter in the description, a global image analysis method according to the invention advantageously makes it possible to immediately and globally assess the content of the analysis image. In particular, it is possible to globally assess a dental situation and, for example, deduce therefrom the need to consult an orthodontist.

Definitions

A "patient" is a person for whom a method according to the invention is implemented, independently of whether or not this person is following an orthodontic treatment.

"Orthodontist" should be understood to mean any person qualified to provide dental care services, which also includes a dentist.

A "dental part", in particular "orthodontic part", should be understood to mean all or part of a dental, in particular orthodontic, appliance.

An orthodontic part may in particular be an orthodontic aligner. Such an aligner extends in such a way as to follow the successive teeth of the arch on which it is fixed. It defines a generally "U" shaped channel, the shape of which is determined to ensure the fixing of the aligner onto the teeth, but also as a function of a desired target positioning for the teeth. More specifically, the shape is determined in such a way that, when the aligner is in its service position, it exerts stresses tending to move the teeth being treated to their target positioning, or to hold the teeth in this target positioning.

The "service position" is the position in which the dental or orthodontic part is worn by the patient.

"Model" should be understood to be a digital three-dimensional model. An arrangement of tooth models is therefore a model.

"Image" should be understood to be an image in two dimensions, like a photograph or an image taken from a film. An image is formed by pixels.

A "reference image" is a view of a "reference" model.

"Image of an arch" or "model of an arch" should be understood to be a representation of all or part of said arch. Such a representation is preferably in colors.

The "acquisition conditions" of an image specify position and the orientation in space of an acquisition apparatus acquiring this image in relation to the teeth of the patient (real acquisition conditions) or to a model of teeth of the patient (virtual acquisition conditions), and preferably the calibration of this acquisition apparatus. Acquisition conditions are said to be "virtual" when they correspond to a simulation in which the acquisition apparatus would be in said acquisition conditions (theoretical positioning and preferably calibration of the acquisition apparatus) relative to a model.

In virtual conditions of acquisition of a reference image, the acquisition apparatus may be also qualified as "virtual". The reference image is in fact acquired by a hypothetical acquisition apparatus, having the characteristics of the "real" acquisition apparatus used for the acquisition of the real images, and in particular of the updated images.

The "calibration" of an acquisition apparatus is made up of all the values of the calibration parameters. A "calibration parameter" is a parameter intrinsic to the acquisition apparatus (unlike its position and orientation) whose value influences the image acquired. Preferably, the calibration parameters are chosen from the group formed by the diaphragm aperture, the exposure time, the focal distance and the sensitivity.

A "discriminating information item" is a characteristic feature which may be extracted from an image ("image feature"), conventionally by computer processing of this image.

A discriminating information item may exhibit a variable number of values. For example, a contour feature may be equal to 1 or 0 depending on whether a pixel belongs or does not belong to a contour. A brightness feature may take a large number of values. The processing of the image makes it possible to extract and quantify the discriminating information item.

The discriminating information item may be represented in the form of a "map". A map is thus the result of a processing of an image in order to reveal the discriminating information item, for example the contour of the teeth and of the gums.

"Match" or "fit" between two objects designates a measurement of the difference between these two objects. A match is maximal ("best fit") when it results from an optimization making it possible to minimize said difference.

An object modified to obtain a maximum match may be qualified as "optimal" object.

Two images or "views" which exhibit a maximal match represent substantially at least one same tooth, in the same way. In other words, the representations of the tooth on these two images may be substantially superimposed.

The search for a reference image exhibiting a maximal match with an updated image is performed by searching for the virtual acquisition conditions of the reference image exhibiting a maximal match with the real acquisition conditions of the updated image.

By extension, a model exhibits a maximal match with an image when this model has been chosen from several models because it allows a view exhibiting a maximal match with said image and/or when this image has been chosen from several images because it exhibits a maximal match with a view of said model.

In particular, an updated image is in maximal match with a reference model when a view of this reference model provides a reference image showing a maximal match with the updated image.

The comparison between two images results preferably from the comparison of two corresponding maps. "Distance" is used conventionally to denote a measurement of the difference between two maps or between two images.

The "metaheuristic" methods are known optimization methods. They are preferably chosen from the group formed by evolutionary algorithms, preferably chosen from: evolution strategies, genetic algorithms, differential evolution algorithms, distribution estimation algorithms, artificial immunity systems, shuffled complex evolution path recomposition, simulated annealing, ant colony algorithms, particular swarm optimization algorithms, search with taboos, and the GRASP method;

the kangaroo algorithm, the Fletcher and Powell method, the sound effects method, stochastic tunneling, random-restart hill climbing, the cross-entropy method, and the hybrid methods between the abovementioned metaheuristic methods.

"Description" of an image denotes information particularly relating to the definition of the tooth zones of this image and to the tooth attribute values which are associated with them, and/or relating to an image attribute value of said image. The number of possible values for a tooth attribute or an image attribute is unlimited.

A "historical" image is an image of a dental arch enriched with a description. The tooth zones of a historical image are qualified as "historical tooth zones".

"Comprising" or "including" or "exhibiting" should be interpreted without restriction, unless indicated otherwise.

BRIEF DESCRIPTION OF THE FIGURES

Other features and advantages of the invention will become more apparent on reading the following detailed description and studying the attached drawing in which.

DETAILED DESCRIPTION

A detailed analysis method according to the invention requires the creation of a learning base. This creation preferably implements a method comprising the steps A) to F), or, in one embodiment, in place of the steps A) to C), preferably the steps A') to C').

First Main Embodiment of the Enrichment Method

The step A) is intended for the production of an updated reference model modeling an arch of the patient. It preferably comprises one or more of the features of the step a) of WO 2016 066651, incorporated by reference, to produce an initial reference model.

The updated reference model is preferably created with a 3D scanner. Such a so-called "3D" model may be observed from any angle. An observation of the model, from a determined angle and distance, is called a "view" or "reference image".

Figure 1:
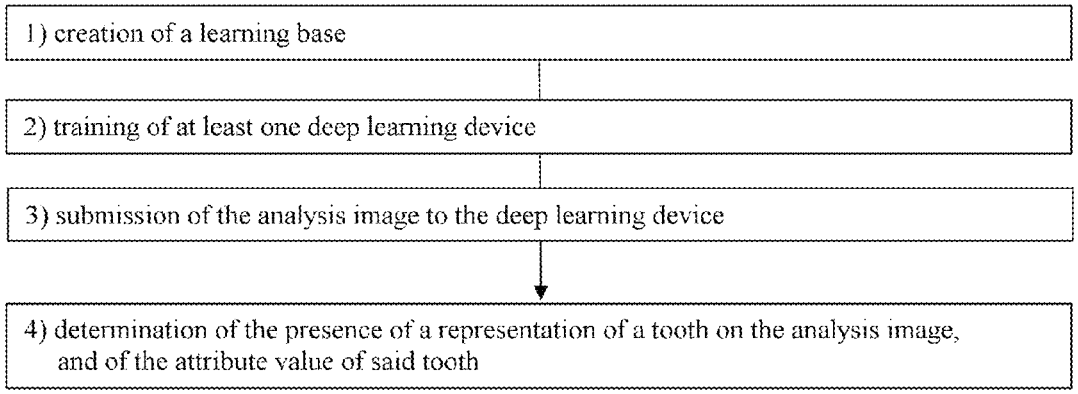
FIG. 1 represents, schematically, the different steps of a method for detailed analysis of an image, according to the invention.
Figure 2:
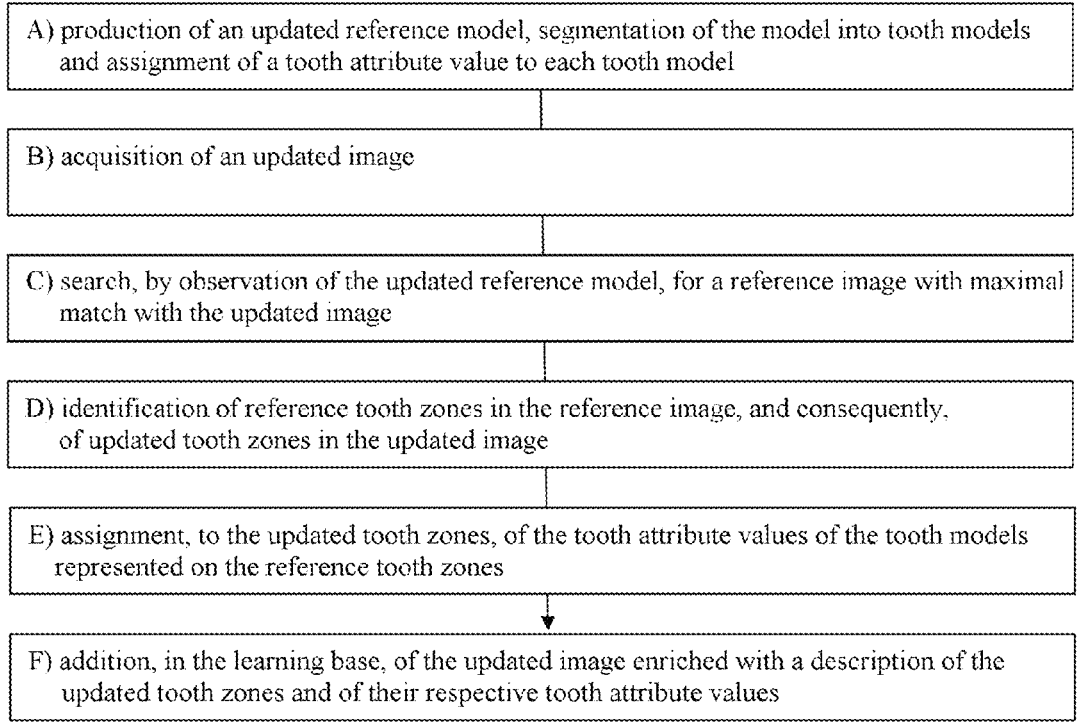
FIG. 2 represents, schematically, the different steps of a method for enriching a learning base, according to the invention.
Figure 3:
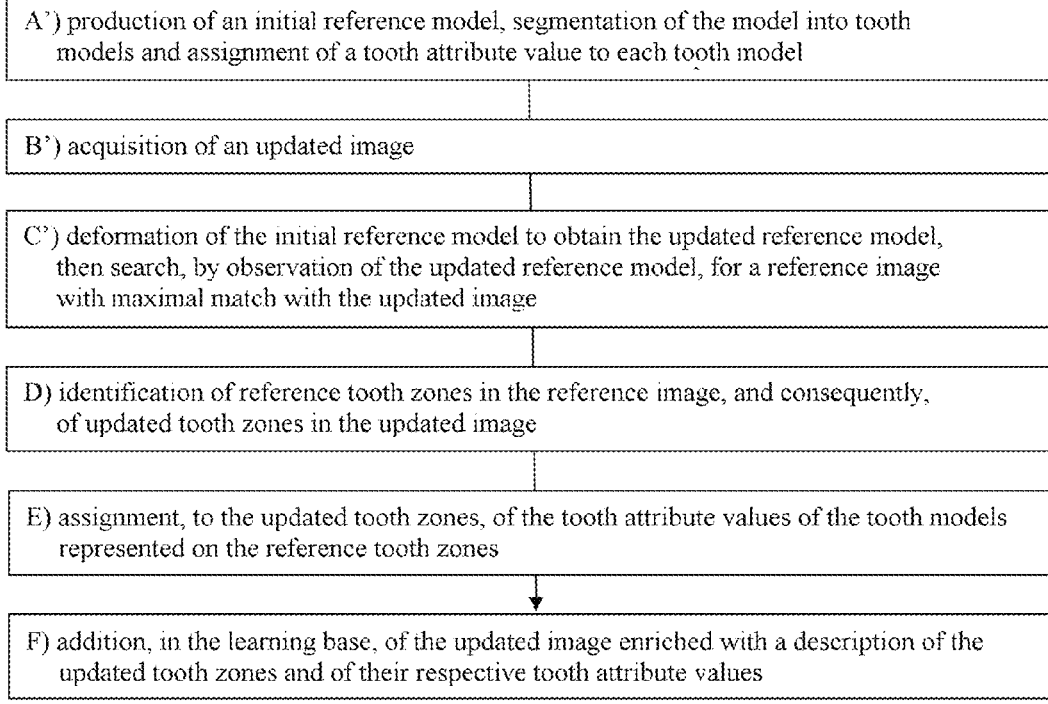
FIG. 3 represents, schematically, the different steps of a variant of a method for enriching a learning base, according to the invention.
Figure 4:
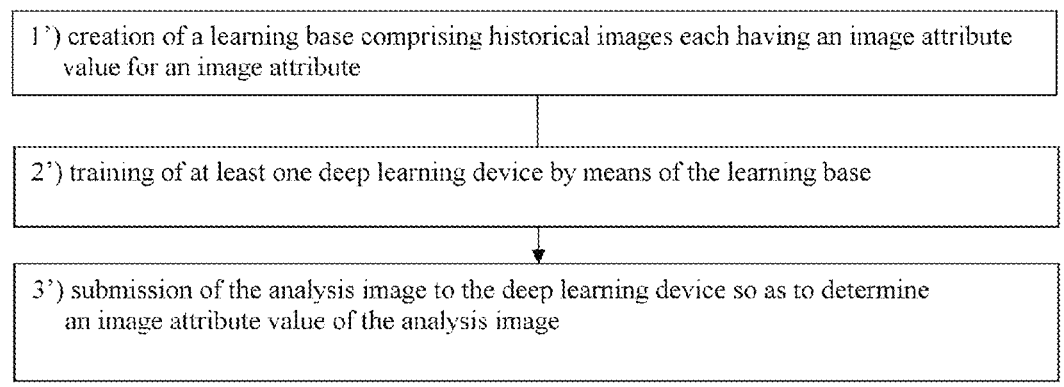
FIG. 4 represents, schematically, the different steps of a method for global analysis of an image, according to the invention.
Figure 5:
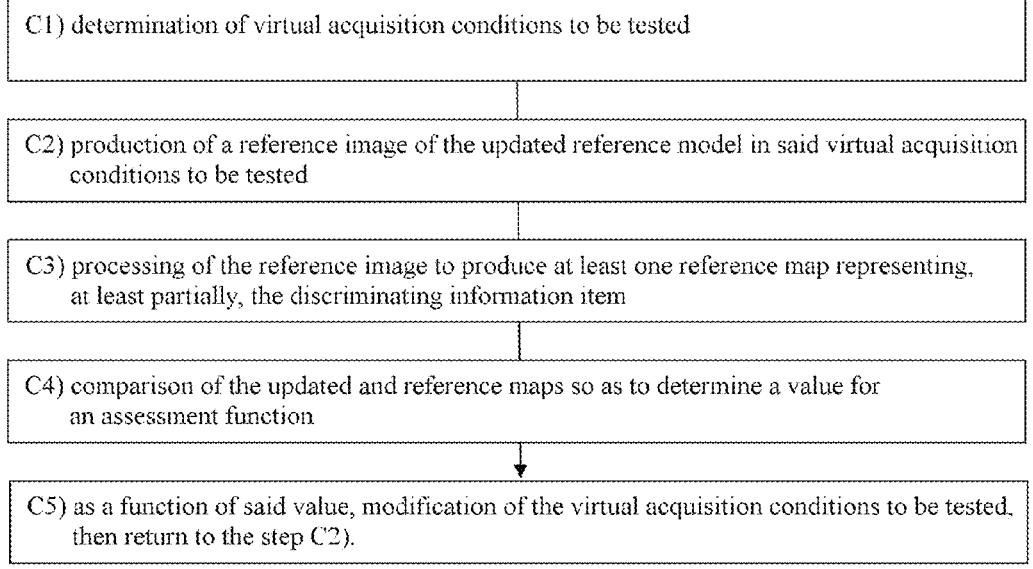
FIG. 5 represents, schematically, the different steps of a step C) of a method for enriching a learning base, according to the invention.
Figure 6:
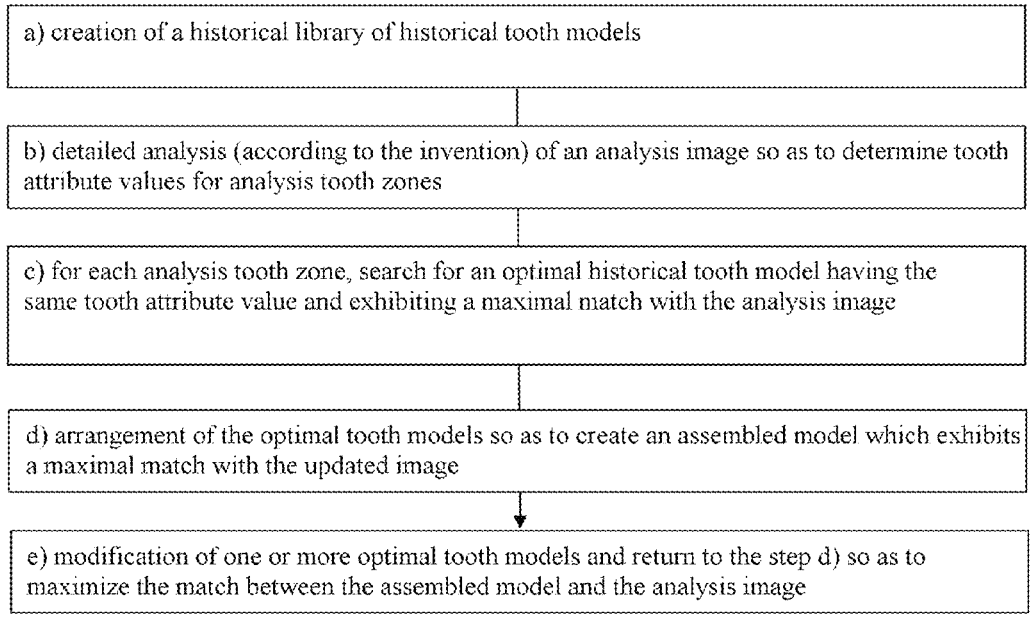
FIGS. 6 and 18 represent, schematically, the different steps of a method for modeling the dental arch of a patient, according to the invention.
Figure 7:
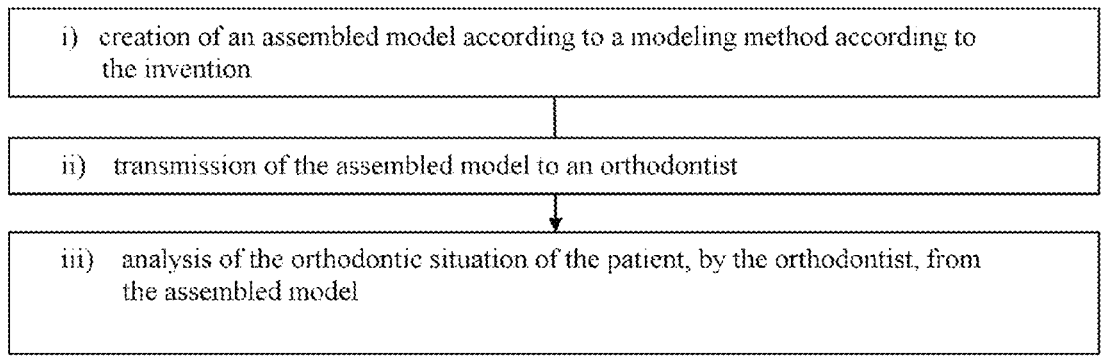
FIG. 7 represents, schematically, the different steps of a method for assessing a dental situation of a patient, according to the invention.
Figure 8:
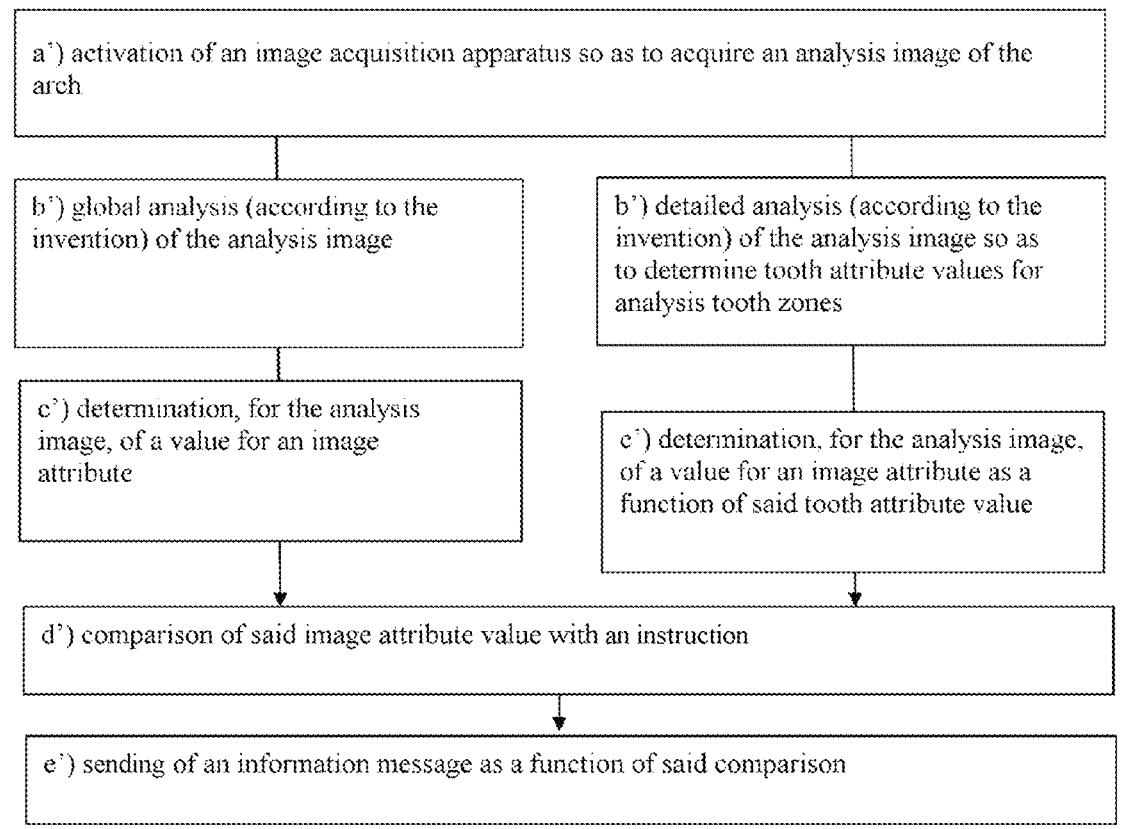
FIG. 8 represents, schematically, the different steps of a method for acquiring an image of a dental arch of a patient, according to the invention.
Figure 9:
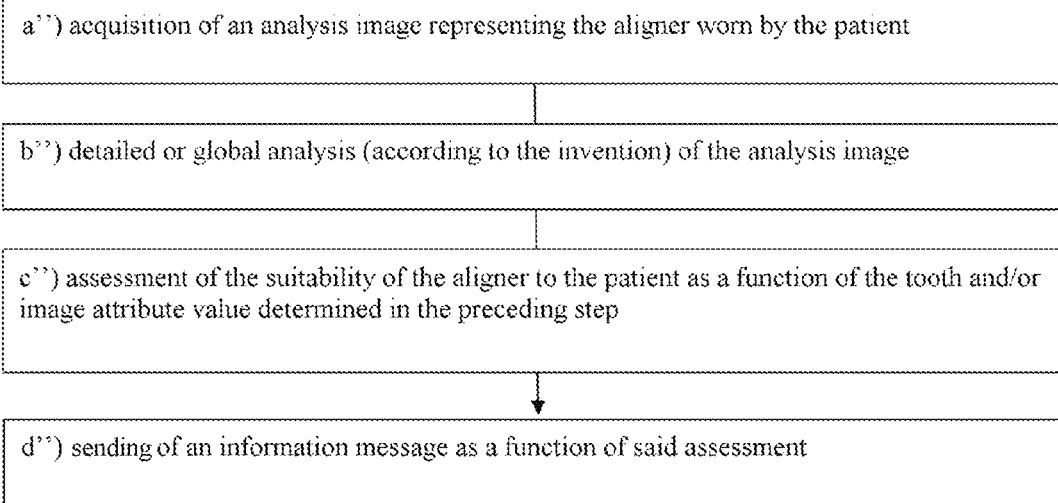
FIG. 9 represents, schematically, the different steps of a method for assessing the shape of an orthodontic aligner of a patient, according to the invention.
Figure 10:
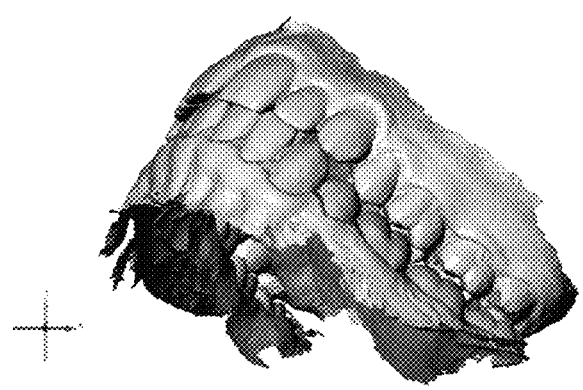
FIG. 10 represents an example of a reference image of an initial reference model.
Figure 11A:
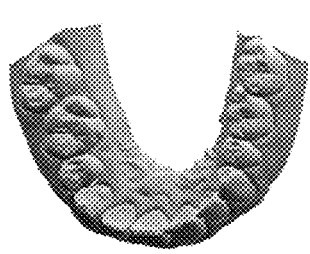
FIG. 11 (11a-11d) illustrates a way of processing to determine the tooth models in an initial reference model, as described in WO 2016 066651.

FIG. 11a is an example of reference image.

The updated reference model may be prepared from measurements performed on the teeth of the patient or on a molding of his or her teeth, for example a plaster molding.

Figure 11B:
Figure 11C:
Figure 11D:
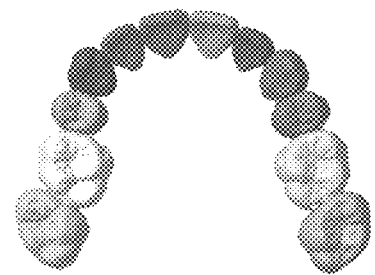

For each tooth, from the updated reference model, a model of said tooth, or "tooth model", is defined (FIG. 11d). This operation, known per se, is called "segmentation" of the updated reference model.

In the updated reference model, a tooth model is preferably delimited by a gingival margin which may be broken down into an interior gingival margin (of the side of the interior of the mouth relative to the tooth), an exterior gingival margin (oriented toward the outside of the mouth relative to the tooth) and two lateral gingival margins.

One or more tooth attributes are associated with the tooth models as a function of the teeth that they model.

The tooth attribute is preferably chosen from a tooth number, a tooth type, a tooth shape parameter, for example a tooth width, in particular a mesio-palatine width, a thickness, a crown height, an index of mesial and distal deflection of the incisive margin, or a level of abrasion, a tooth appearance parameter, in particular a translucency index or a color parameter, a parameter relating to the condition of the tooth, for example "abraded", "broken", "decayed" or "fitted" (that is to say in contact with a dental, preferably orthodontic, appliance), an age for the patient, or a combination of these attributes. A tooth attribute is preferably an attribute which only relates to the tooth modeled by the tooth model.

A tooth attribute value may be assigned to each tooth attribute of a particular tooth model.

For example, the "tooth type" tooth attribute will have the value "incisor", "canine" or "molar" depending on whether the tooth model is that of an incisor, of a canine or of a molar, respectively.

The assignment of the tooth attribute values to the tooth models may be manual or, at least partly, automatic. For example, if the value of a tooth attribute is identical whatever the tooth model, such as for the "age of the patient" tooth attribute, it may be sufficient to assign a value to one tooth model to determine the value of this attribute for the other tooth models.

Similarly, the tooth numbers are conventionally assigned according to a standard rule. It is therefore sufficient to know this rule and the number of a tooth modeled by a tooth model to calculate the numbers of the other tooth models.

In a preferred embodiment, the shape of a particular tooth model is analyzed so as to define its tooth attribute value, for example its number. This shape recognition is preferably performed by means of a deep learning device, preferably a neural network. Preferably, a library of historical tooth models is created, each historical tooth model having a value for the tooth attribute, as described hereinbelow (step a)), the deep learning device is trained with views of the historical tooth models of this library, then one or more views of the particular tooth model are analyzed with the trained deep learning device, so as to determine the tooth attribute value of said particular tooth model.

The allocation of the tooth attribute values may then be performed totally without human intervention.

The step B) is intended for the acquisition of one or preferably several updated images.

The step B) preferably comprises one or more of the features of the step b) of WO 2016 066651.

The acquisition of the updated images is performed by means of an image acquisition apparatus, preferably chosen from a cellphone, a so-called "connected" camera, a so-called "smart" watch, a tablet or a personal computer, fixed or portable, comprising an image acquisition system such as a webcam or a camera. Preferably, the image acquisition apparatus is a cellphone.

Also preferably, the image acquisition apparatus is separated from the dental arch by more than 5 cm, more than 8 cm, even more than 10 cm, which avoids the condensation of steam on the optic of the image acquisition apparatus and facilitates the focusing. Furthermore, preferably, the image acquisition apparatus, in particular the cellphone, has no specific optic for the acquisition of the updated images, which is notably possible because of the separation of the dental arch during the acquisition.

Preferably, an updated image is a photograph or an image extracted from a film. It is preferably in color, preferably in real colors.

Preferably, the acquisition of the updated image or images is performed by the patient, preferably without the use of a support which is bearing on the ground and is immobilizing the image acquisition apparatus, and in particular without tripod.

In one embodiment, the triggering of the acquisition is automatic, that is to say without the action of an operator, as soon as the acquisition conditions are approved by the image acquisition apparatus, in particular when the image acquisition apparatus has determined that it observes a dental arch and/or a retractor and that the conditions of observation are satisfactory (sharpness, brightness, even dimensions of the representation of the dental arch and/or of the retractor).

The time interval between the steps A) and B) is as short as possible in order for the teeth not to be substantially displaced between the production of the updated model and the acquisition of the updated images. Reference images matching with the updated images may then be acquired by observing the updated reference model.

Figure 12A:
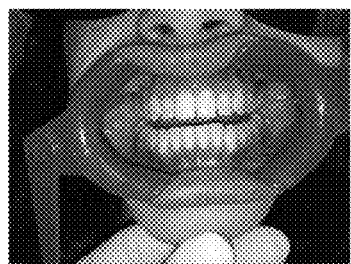
FIG. 12 (12a-12d) illustrates the acquisition of an image by means of a retractor, an operation of cropping of this image, and the processing of an updated image making it possible to determine the contour of the teeth, as described in WO 2016 066651.

Preferably, a dental retractor 10 is used in the step B), as represented in FIG. 12a. The retractor conventionally comprises a support provided with a rim extending around an opening and arranged in such a way that the lips of the patient may rest thereon leaving the teeth of the patient apparent through said opening.

In the step C), the updated reference model is explored to find, for each updated image, a reference image exhibiting a maximal match with the updated image.

The step C) may comprise one or more of the features of the steps c), d) and e) of WO 2016 066651, in as much as they concern such an exploration.

For each updated image, a set of virtual acquisition conditions approximating the real acquisition conditions upon the acquisition of said updated image is preferably determined, roughly. In other words, the position of the image acquisition apparatus is estimated in relation to the teeth at the moment when it took the updated image (position of the acquisition apparatus in space and orientation of this apparatus). This rough assessment advantageously makes it possible to limit the number of tests on virtual acquisition conditions in subsequent operations, and therefore makes it possible to considerably speed up these operations.

To perform this rough assessment, one or more heuristic rules are preferably used. For example, preferably, virtual acquisition conditions likely to be tested in subsequent operations, the conditions which correspond to a position of the image acquisition apparatus behind the teeth or at a distance from the teeth greater than 1 m, are excluded.

Figure 13:
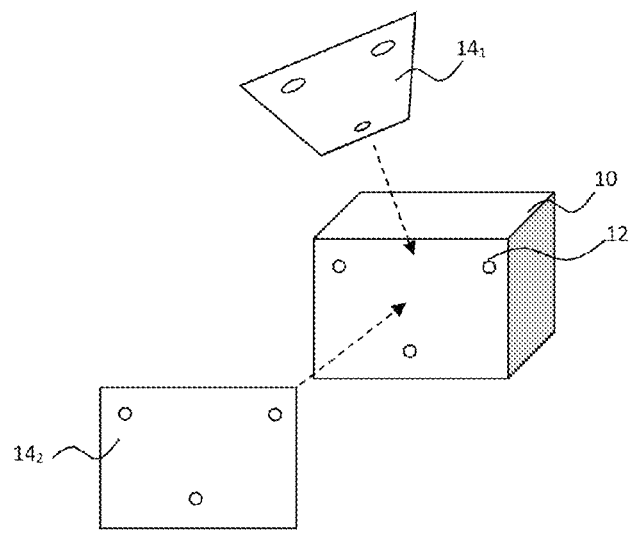
FIG. 13 schematically illustrates the relative position of registration marks 12 of a retractor 10 on updated images 141 and 142, according to the directions of observation represented by broken lines.

In a preferred embodiment, as illustrated in FIG. 13, registration marks are used that are represented on the updated image, and in particular registration marks 12 of the retractor, to determine a region of the space that is substantially conical delimiting virtual acquisition conditions likely to be tested in subsequent operations, or "test cone".

More specifically, at least three registration marks 12 are preferably positioned non-aligned on the retractor 10, and their relative positions on the retractor are accurately measured.

The registration marks are then marked on the updated image, as described previously. Simple trigonometric calculations make it possible to determine approximately the direction from which the updated image was taken.

Next, for each updated image, a reference image is sought that exhibits a maximum match with the updated image. This search is preferably performed by means of a meta-heuristic method, preferably evolutionist, preferably by simulated annealing.

Preferably, at any instant before the step C4), the updated image is analyzed so as to produce an updated map representing, at least partially, a discriminating information item. The updated map therefore represents the discriminating information item in the reference frame of the updated image.

The discriminating information item is preferably chosen from the group consisting of a contour information item, a color information item, a density information item, a distance information item, a brightness information item, a saturation information item, information on reflections and combinations of these information items.

A person skilled in the art knows how to process an updated image to reveal the discriminating information item.

Figure 12B:
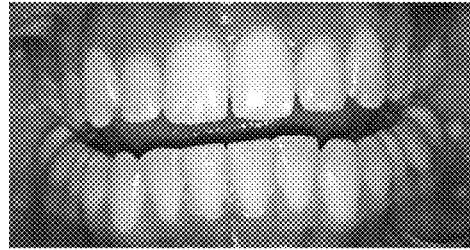
Figure 12C:
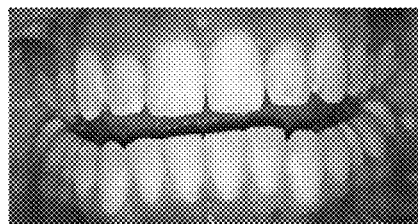
Figure 12D:
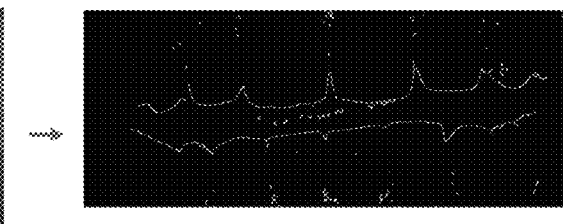

For example, FIG. 12d is an updated map relating to the contour of the teeth obtained from the updated image of FIG. 12b.

Said search comprises the following steps:
C1) determination of virtual acquisition conditions "to be tested";
C2) production of a reference image of the updated reference model in said virtual acquisition conditions to be tested;
C3) processing of the reference image to produce at least one reference map representing, at least partially, the discriminating information item;
C4) comparison of the updated and reference maps so as to determine a value for an assessment function, said value for the assessment function depending on the differences between said updated and reference maps and corresponding to a decision to continue or stop the search for virtual acquisition conditions approximating said real acquisition conditions with greater accuracy than said virtual acquisition conditions to be tested determined in the last occurrence of the step C1);
C5) if said value for the assessment function corresponds to a decision to continue said search, modification of the virtual acquisition conditions to be tested, then return to the step C2).

The step C1) begins with a determination of the virtual acquisition conditions to be tested, that is to say a virtual position and orientation likely to correspond to the real position and orientation of the acquisition apparatus upon the capture of the updated image, but also, preferably, a virtual calibration likely to correspond to the real calibration of the acquisition apparatus upon the capture of the updated image.

The first virtual acquisition conditions to be tested are preferably virtual acquisition conditions assessed roughly, as described previously.

In the step C2), the image acquisition apparatus is then virtually configured in the virtual acquisition conditions to be tested in order to acquire a reference image of the updated reference model in these virtual acquisition conditions to be tested. The reference image therefore corresponds to the image that the image acquisition apparatus would have taken if it had been placed, relative to the updated reference model, and optionally calibrated, in the virtual acquisition conditions to be tested.

If the updated image was taken substantially at the same moment as the updated reference model was created by a scan of the teeth of the patient, the position of the teeth on the updated image is substantially identical to that in the updated reference model. If the virtual acquisition conditions to be tested are exactly the real acquisition conditions, the reference image may therefore be exactly superimposed on the updated image. The differences between the updated image and the reference image result from errors in the assessment of the virtual acquisition conditions to be tested, if they do not correspond exactly to the real acquisition conditions.

In the step C3), the reference image is processed as the updated image so as to produce, from the reference image, a reference map representing the discriminating information item (FIGS. 11a and 11b). A person skilled in the art knows how to process a reference image to reveal the discriminating information item.

In the step C4), the updated and reference maps, both relating to the same discriminating information item, are compared and the difference or "distance" between these two maps is assessed by means of a score. For example, if the discriminating information item is the contour of the teeth, the mean distance between the points of the contour of the teeth which appears on the reference image and the points of the corresponding contour which appears on the updated image may be compared, the score being all the higher when this distance is small.

The score may for example be a correlation coefficient.

Preferably, the virtual acquisition conditions comprise the calibration parameters of the acquisition apparatus. The score is that much higher when the values of the calibration parameters tested are close to the calibration parameter values of the acquisition apparatus used upon the acquisition of the updated image. For example, if the diaphragm aperture tested is far from that of the acquisition apparatus used upon the acquisition of the updated image, the reference image shows fuzzy regions and sharp regions which do not correspond to the fuzzy regions and to the sharp regions of the updated image. If the discriminating information item is the contour of the teeth, the updated and reference maps will not therefore represent the same contours and the score will be low.

The score is then assessed by means of an assessment function. The assessment function makes it possible to decide whether the cycling on the steps C1) to C5) must be continued or stopped. The assessment function may for example be equal to 0 if the cycling must be stopped or be equal to 1 if the cycling must continue.

The value of the assessment function may depend on the score achieved. For example, a decision may be made to continue the cycling if the score does not exceed a threshold. For example, if an exact match between the updated and reference images leads to a score of 100%, the threshold may be, for example, 95%. Obviously, the higher the threshold, the better will be the accuracy of the assessment of the virtual acquisition conditions if the score manages to exceed this threshold.

The value of the assessment function may also depend on scores obtained with virtual acquisition conditions tested previously.

The value of the assessment function may also depend on random parameters and/or on the number of cycles already performed.

In particular, it is possible, despite the repetition of the cycles, not to manage to find virtual acquisition conditions which are sufficiently close to the real acquisition conditions for the score to reach said threshold. The assessment function may then lead to the decision to exit the cycle even through the best score obtained has not reached said threshold. This decision may result, for example, from a number of cycles greater than a predetermined maximum number.

A random parameter in the assessment function may also authorize the continuation of tests of new virtual acquisition conditions, even though the score appears satisfactory.

The assessment functions conventionally used in the metaheuristic optimization, preferably evolutionist, methods, particularly in the simulated annealing methods, may be used for the assessment function.

In the step C5), if the value of the assessment function indicates a decision to continue the cycling, the virtual acquisition conditions to be tested are modified and the cycling recommences on the steps C1) to C5), consisting in producing a reference image and a reference map, in comparing the reference map with the updated map to determine a score, then in taking a decision as a function of this score.

The modification of the virtual acquisition conditions to be tested corresponds to a virtual displacement in space and/or to a modification of the orientation and/or, preferably, to a modification of the calibration of the acquisition apparatus. This modification may be random, preferably such that the new virtual acquisition conditions to be tested still belong to the set determined upon the rough assessment. The modification is preferably guided by heuristic rules, for example by favoring the modifications which, according to an analysis of the preceding scores obtained, appear most favorable for increasing the score.

The cycling is continued until the value of the assessment function indicates a decision to cease this cycling and to continue to the step D), for example if the score reaches or exceeds said threshold.

The optimization of the virtual acquisition conditions is preferably performed by using a metaheuristic, preferably evolutionist, method, preferably a simulated annealing algorithm. Such an algorithm is well known for nonlinear optimization.

If the cycling has been exited without a satisfactory score having been able to be obtained, for example without the score having been able to reach said threshold, the method may be stopped (failure situation) or a new step C) may be launched, with a new discriminating information item and/or with a new updated image. The method may also be continued with the virtual acquisition conditions corresponding to the best score reached. A warning may be emitted in order to inform the user of the error on the result.

If the cycling has been exited when a satisfactory score has been able to be obtained, for example because the score has reached, even exceeded said threshold, the virtual acquisition conditions correspond substantially to the real acquisition conditions of the updated image.

Preferably, the virtual acquisition conditions comprise the calibration parameters of the acquisition apparatus. The method thus makes it possible to assess the values of these parameters without it being necessary to know the nature of the acquisition apparatus or its setting. The acquisition of the updated images may therefore be performed without any particular precautions, for example by the patient him or herself by means of his or her cellphone.

In addition, the search for the real calibration is performed by comparing an updated image with views of a reference model in virtual acquisition conditions to be tested. Advantageously, it does not require the updated image to show a standard calibration gauge, that is to say a gauge whose characteristics are accurately known making it possible to determine the calibration of the acquisition apparatus.

The step C) therefore culminates in the determination of virtual acquisition conditions exhibiting a maximal match with the real acquisition conditions. The reference image therefore exhibits a maximal match with the updated image, that is to say that these two images may substantially be superimposed.

In one embodiment, said search of the virtual acquisition conditions in the step C) is performed by using a meta-heuristic, preferably evolutionist, method, preferably a simulated annealing algorithm.

In the step D), the reference tooth zones are identified on the reference image and they are transferred to the updated image to define corresponding updated tooth zones.

In particular, the reference image is a view of the updated reference model segmented into tooth models. The limits of the representation of each tooth model on the reference image, or "reference tooth zone", may therefore be identified.

The superimposition of the updated and reference images then makes it possible to transfer the limits of the reference tooth zones to the updated image, and thus define the updated tooth zones. Since the reference image exhibits a maximal match with the updated image, the updated tooth zones therefore substantially define the limits of the tooth models represented on the reference image.

In the step E), each updated tooth zone is assigned the tooth attribute value or values of the tooth model which corresponds to it.

In particular, the reference image is a view of the updated reference model in which the tooth models have been assigned respective tooth attribute values for at least one tooth attribute, for example a tooth number. Each reference tooth zone may therefore inherit the tooth attribute value of the tooth model that it represents. Each updated tooth zone may then inherit the tooth attribute value of the reference tooth zone which allowed it to be defined.

At the end of the step E), an updated image and a description of the updated image is therefore obtained that defines one or more updated tooth zones and, for each of these zones, a tooth attribute value for at least one tooth attribute, for example a tooth number.

The updated image enriched with its description is called "historical image".

Figure 17A:
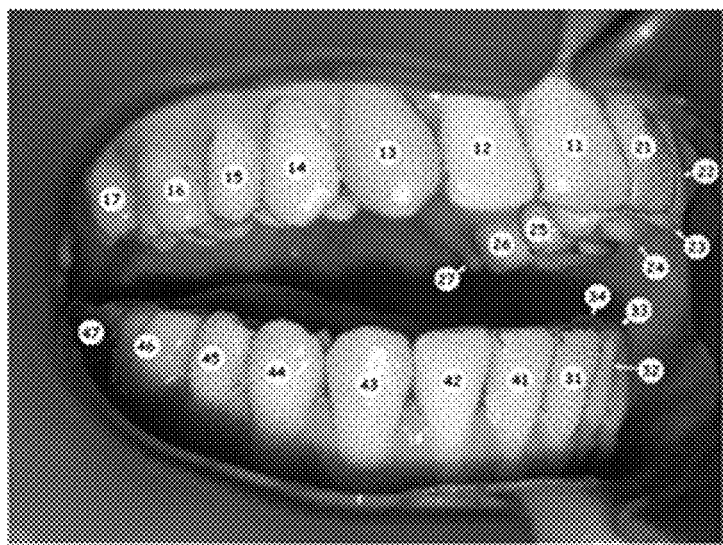
FIGS. 17 (17a-17c) illustrates an enrichment method according to the invention.
Figure 17B:
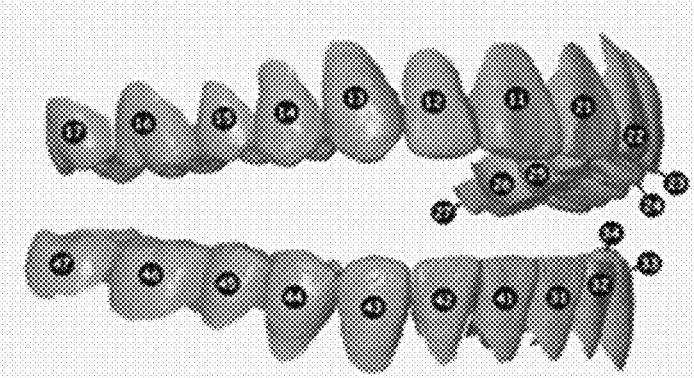
Figure 17C:
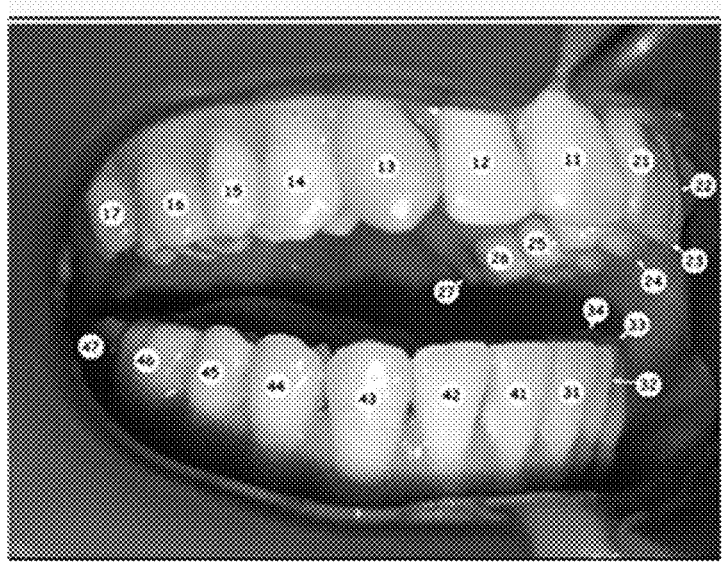

FIG. 17a shows an example of updated image (acquired in the step B)) being analyzed in order to determine the contours of the teeth. FIG. 17b shows the reference image exhibiting a maximal match with the updated image (resulting from the step C)). The numbers of the teeth are displayed on the corresponding teeth. FIG. 17c illustrates the transfer of the tooth numbers to the updated tooth zones (step D) and E)).

In the step F), the historical image is added to the learning base.

The steps A) to F) are preferably performed for more than 1000, more than 5000, or more than 10 000 different patients, or "historical patients".

As now clearly emerges, the invention provides a method that is particularly effective for creating a learning base.

The invention relates also to a method for training a deep learning device, preferably a neural network, said method comprising an enrichment of a learning base according to a method comprising steps A) to F) so as to acquire a plurality of historical images, then the use of said learning base to train said deep learning device.

Second Main Embodiment of the Enrichment Method

The invention is not however limited to the embodiments described above.

In particular, the updated reference model is not necessarily the direct result of a scan of the arch of the patient. The updated reference model may in particular be a model obtained by deformation of an initial reference model which is itself resulting directly from such a scan.

The method then comprises, preferably, in place of the steps A) to C), the steps A') to C').

The step A') is identical to the step A). In the step A'), the reference model generated is however intended to be modified. It is therefore qualified as "initial reference model", and not as "updated reference model", as according to the step A).

The initial reference model may in particular be generated at an initial instant preceding an active orthodontic treatment, for example less than 6 months, less than 3 months, or less than 1 month before the start of the treatment. The steps B') to C') may then be implemented to track the trend of the treatment between the initial instant and the updated instant of the step B').

The initial instant may alternatively be an instant at the end of active orthodontic treatment, for example less than 6 months, less than 3 months, or less than 1 month after the end of the treatment. The steps B') to C') may then be implemented to monitor the appearance of any recurrence.

The step B') is identical to the step B). In the step B'), the updated images are however also intended to guide the modification of the initial reference model to define the updated reference model, in the step C').

The time interval between the steps A') and B') is not limited, since, as explained hereinbelow, the initial reference model will be deformed to obtain an updated reference model with maximal match with the updated images. The time interval between the steps A') and B') may for example be greater than 1 week, than 2 weeks, than 1 month, than 2 months or more than 6 months.

The step C') is more complex than the step C) since the search for a reference image exhibiting a maximal match with an updated image is not limited to searching for the optimal virtual acquisition conditions. It also includes a search for an updated reference model, that is to say a reference model in which the teeth have substantially the same position as on the updated image.

Figure 16:
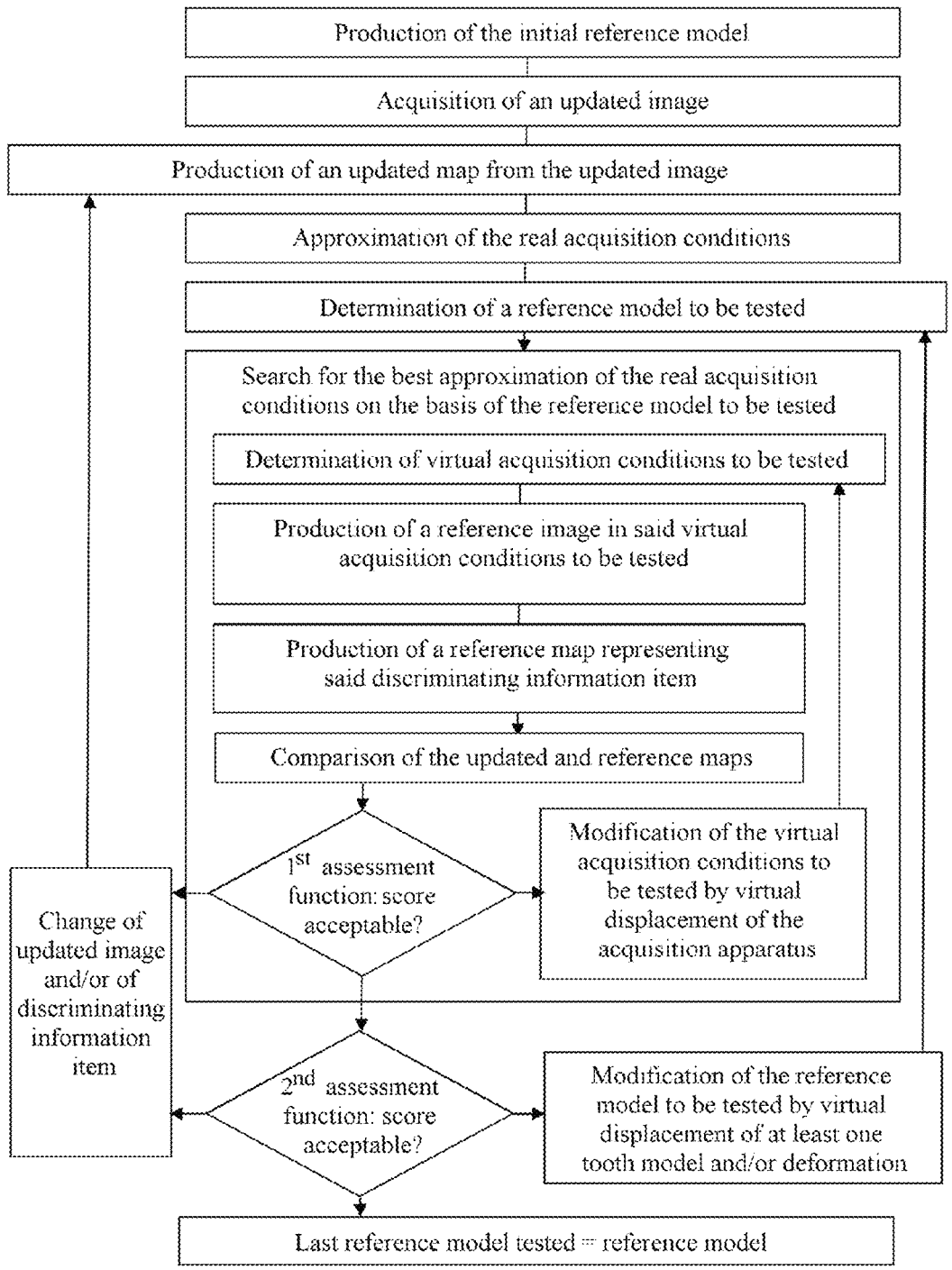
FIG. 16 illustrates the step e) described in WO 2016 066651.

The step C') preferably comprises one or more of the features of the steps c), d) and e) of WO 2016 066651, and in particular of the step e) illustrated in FIG. 16.

The objective is to modify the initial reference model until an updated reference model is obtained which exhibits a maximal match with the updated image. Ideally, the updated reference model is therefore a model of the arch from which the updated image would have been able to be taken if this model had been the arch itself.

A succession of reference models "to be tested" is therefore tested, the choice of a reference model to be tested preferably being dependent on the level of correspondence of the reference models "to be tested" previously tested with the updated image.

Preferably, the search comprises, for an updated image,
a first optimization operation making it possible to search, in a reference model to be tested determined from the initial reference model, for virtual acquisition conditions best corresponding to the real acquisition conditions of the updated image, and
a second optimization operation making it possible to search, by testing a plurality of said reference models to be tested, for the reference model best corresponding to the positioning of the teeth of the patient upon the acquisition of the updated image.

Preferably, a first optimization operation is performed for each test of a reference model to be tested during the second optimization operation.

Preferably, the first optimization operation and/or the second optimization operation, preferably the first optimization operation and the second optimization operation, implement a metaheuristic method, preferably evolutionist, preferably a simulated annealing.

The step C') therefore culminates in the determination
- of an updated reference model exhibiting a maximal match with the updated image, and
- virtual acquisition conditions exhibiting a maximal match with the real acquisition conditions.

A method comprising the steps A') to C') may advantageously be implemented in the context of an active or passive orthodontic treatment, or, more generally, to track any changes to the teeth.

In the different methods according to the invention, the enrichment of the learning base does not necessarily result from an enrichment method according to the invention.

In one embodiment, the learning base is created by an operator. The latter thus analyzes thousands of analysis images. For the learning base to be able to be used for the implementation of a detailed analysis method, it determines the tooth zones, then assigns them tooth attribute values. For the learning base to be able to be used for the implementation of a global analysis method, it assigns image attribute values to each image. It may thus form historical images.

Detailed Image Analysis Method

The method for detailed analysis of an "analysis image" of a dental arch of a patient according to the invention comprises the steps 1) to 4).

Preferably, the analysis image, preferably a photograph or an image extracted from a film, preferably in color, preferably in real color, is acquired with an image acquisition apparatus, preferably a cellphone, separated from the dental arch by more than 5 cm, more than 8 cm, even more than 10 cm, and which, preferably, has no other specific optic.

Preferably, the analysis image represents several teeth, preferably more than 2, more than 3, more than 4 or more than 5 teeth of the patient. FIG. 12a or FIG. 12b could be examples of analysis images. The arrangement of the teeth is realistic, i.e. it corresponds to the arrangement which is observed by the image acquisition apparatus when it has acquired the analysis image.

Preferably, the acquisition of the analysis image is performed by the patient, preferably without the use of a support which is bearing on the ground and is immobilizing the image acquisition apparatus, and in particular without tripod.

In one embodiment, the triggering of the acquisition of the analysis image is automatic, that is to say without the action of an operator, as soon as the acquisition conditions are approved by the image acquisition apparatus, in particular when the image acquisition apparatus has determined that it observes a dental arch and/or a retractor and that the observation conditions are satisfactory (sharpness, brightness, even dimensions of the representation of the dental arch and/or of the retractor).

In the step 1), a learning base is created comprising more than 1000, preferably more than 5000, preferably more than 10 000, preferably more than 30 000, preferably more than 000, preferably more than 100 000 historical images. The greater the number of historical images, the better the analysis performed by the method.

Preferably, a learning base is used that is enriched according to an enrichment method according to the invention.

The learning base may however be constructed according to other methods, for example be created manually. To create a historical image of the learning base, an operator, preferably an orthodontist, identifies one or more "historical" tooth zones on an image, called then assigns, to each identified historical tooth zone, a value for at least one tooth attribute.

In step 2), a deep learning device, preferably a neural network, is trained with the learning base.

A "neural network" or "artificial neural network" is a set of algorithms well known to a person skilled in the art.

The neural network may in particular be chosen from:
the networks specializing in the classification of images, called "CNN" ("convolutional neural network"), for example
AlexNet (2012)
ZF Net (2013)
VGG Net (2014)
GoogleNet (2015)
Microsoft ResNet (2015)
Caffe: BAIR Reference CaffeNet, BAIR AlexNet
Torch:VGG_CNN_S,VGG_CNN_M,
VGG_CNN_M_2048,VGG_CNN_M_10
24,VGG_CNN_M_128,VGG_CNN_F,VGG
ILSVRC-2014 16-layer,VGG ILSVRC-2014 19-layer, Network-in-Network (Imagenet & CIFAR-10) Google: Inception (V3, V4).

The networks specializing in the location and detection of objects in an image, the object detection network, for example:
R-CNN (2013)
SSD (Single Shot MultiBox Detector: Object Detection network), Faster R-CNN (Faster Region-based Convolutional Network method: Object Detection network)
Faster R-CNN (2015)
SSD (2015).

The above list is not limiting

In the step 2), the deep learning device is preferably trained by a learning process called "deep learning". By presenting, as input for the deep learning device, historical images (images+descriptions), the deep learning device progressively learns to recognize patterns on an image, and to associate them with tooth zones and with tooth attribute values, for example tooth numbers.

In the step 3), the image that is to be analyzed, or "analysis image", is submitted to the deep learning device.

Through its training in the step 2), the deep learning device is capable of analyzing the analysis image and of recognizing said patterns therein. It may in particular determine a probability relating to:
the presence, at a location in said analysis image, of a zone representing, at least partially, a tooth, or "analysis tooth zone",
the attribute value of the tooth represented on said analysis tooth zone.

For example, it is capable of determining that there is a 95% chance that a form of the analysis image represents an incisor.

Preferably, the deep learning device analyses all the analysis image and determines probabilities for all the analysis tooth zones that it has identified.

In the step 4), the results of the preceding step are analyzed to determine the teeth represented on the analysis image.

When the learning base comprises more than 10 000 historical images, the step 3) gives particularly satisfactory results. In particular, such a learning base makes it possible to establish a probability threshold such that, if a probability associated with an analysis tooth zone and with a tooth attribute value for this analysis tooth zone exceeds said threshold, the analysis tooth zone effectively represents a tooth having said tooth attribute value.

The step 4) thus leads to the definition of an analysis image enriched with a description defining the analysis tooth zones and, for each analysis tooth zone, the values of the attributes of the tooth represented by the analysis tooth zone.

Global Image Analysis Method

The method for global analysis of an updated image of a dental arch of a patient according to the invention comprises the steps 1') to 3').

The method is similar to the detailed analysis method described above, apart from the fact that, according to the global analysis, it is not necessary to analyze the individual situation of each tooth. The analysis is global to all the image. In other words, the deep learning device determines the value of an "image" attribute without having to previously determine tooth attribute values.

For example, the deep learning device may conclude that, "globally", the dental situation is "satisfactory" or "unsatisfactory", without determining the tooth potentially at the origin of the dissatisfaction.

The step 1') is similar to the step 1). The historical images however include a description specifying an image attribute value for each image.

The step 2') is similar to the step 2).

In the step 3'), the analysis image is submitted to the deep learning device.

Through its training in the step 2'), the deep learning device is capable of analyzing the analysis image and of recognizing said patterns therein. Based on these patterns, it may in particular determine a probability relating to the value of the image attribute considered.

Application to the Modeling of a Dental Arch

A detailed analysis method according to the invention is in particular useful for modeling a dental arch, notably for establishing a remote diagnostic.

It is desirable for each to regularly check his or her dentition, particularly in order to check that the position of his or her teeth is not changing for the worse. In an orthodontic treatment, this change for the worse may in particular lead to the treatment being modified. After an orthodontic treatment, a change for the worse, called "recurrence", may lead to a repeat of a treatment. Finally, more generally and independently of any treatment, each may want to track any displacements of his or her teeth.

Conventionally, the checks are performed by an orthodontist who has appropriate apparatus. These checks are therefore costly. Furthermore, the appointments are restrictive. Finally, some people are apprehensive of a visit to an orthodontist and will fail to make an appointment for a simple check or to assess the feasibility of an orthodontic treatment.

US 2009/0291417 describes a method making it possible to create, then modify, three-dimensional models, particularly for the manufacture of orthodontic appliances.

WO 2016 066651 describes a method for checking the positioning and/or the shape and/or the appearance of teeth of a patient. This method comprises a step of creation of an initial reference model of the teeth, at an initial instant, preferably with a 3D scanner, then, at a subsequent instant, or "updated instant", for example six months after the initial instant, the creation of an updated reference model, by deformation of the initial reference model. This deformation is performed in such a way that the updated reference model allows observation substantially identical to images of the teeth acquired at the updated instant, in particular to photos or images from a video taken by the patient him or herself, with no particular precautions, called "updated images".

The updated images are therefore used to modify the initial, very accurate, reference model. The updated reference model which results from the deformation of the initial reference model, guided by the analysis of the updated images, is therefore also very accurate.

The method described in WO 2016/66651 does however require an appointment with the orthodontist in order to create the initial reference model. This appointment constitutes a brake to prevention. In effect, a patient will not necessarily consult an orthodontist if he or she does not perceive the need therefor. In other words, the method is often implemented only if a malocclusion is found and has to be corrected.

There is therefore a need for a method that addresses this problem, by facilitating prevention. One aim of the invention is to address this need.

To this end, the invention proposes a method for modeling a dental arch of a patient, said method comprising the following steps:

a) creation of a historical library comprising more than 1000 tooth models, called "historical tooth models", and assignment to each historical tooth model of a value for at least one tooth attribute, or "tooth attribute value";

b) analysis of at least one "analysis image" of the dental arch according to a detailed analysis method according to the invention, so as to determine at least one analysis tooth zone and at least one tooth attribute value associated with said analysis tooth zone;

c) for each analysis tooth zone determined in the preceding step, search, in the historical library, for a historical tooth model exhibiting a maximum proximity with the analysis image or with the analysis tooth zone, or "optimal tooth model";

d) arrangement of all the optimal tooth models so as to create a model which exhibits a maximal match with the updated image, or "assembled model";

e) optionally, replacement of at least one optimal tooth model by another historical tooth model and repeat of the step d) so as to maximize the match between the assembled model and the analysis image;

f) optionally, repeat of the step b) with another analysis image and, in the step d) and/or e), search for a maximal match with all the analysis images used.

The invention thus makes it possible, from a simple analysis image, for example a photograph taken by means of a cellphone, to reconstruct, with a good reliability, a dental arch in the form of an assembled model. In particular, the analysis image may be acquired as described here above at step 1).

Obviously, the analysis of a single analysis image is insufficient to generate an assembled model which accurately corresponds to the arrangement of the teeth of the patient. Such an accuracy is however not generally essential for performing a first diagnosis of the dental situation of the patient.

Moreover, the accuracy of the assembled model may be increased if several analysis images are processed.

The steps b) to c) are preferably implemented for several analysis images and, in the steps d) and e), the optimal tooth models and an assembled model are searched so as to obtain a maximal match in light of all the analysis images (step f)).

The invention also relates to a method for assessing a dental situation of a patient, comprising the following steps:

i) creation of an assembled model according to a modeling method according to the invention;
ii) transmission of the assembled model to a recipient, preferably an orthodontist and/or a computer;
iii) analysis of the orthodontic situation of the patient, by the recipient, from the assembled model;
iv) preferably, informing of the patient of the orthodontic situation, preferably, via his or her cellphone.

The patient may therefore very easily ask an orthodontist to check his or her dental situation, without even having to travel, by simply transmitting one or preferably several photos of his or her teeth.

A modeling method is now described in detail.

In the step a), a historical library 20 (FIG. 18) is created comprising more than 1000, preferably more than 5000, preferably more than 10 000 historical tooth models 22. The greater the number of historical tooth models, the more accurate the assembled model.

A historical tooth model can in particular be obtained from a model of a dental arch of a "historical" patient obtained with a scanner. This arch model may be segmented in order to isolate the representations of the teeth, as in FIG. 11*d*. Each of these representations, exhibiting a specific gray shade in FIG. 11*d*, can constitute a historical tooth model.

Preferably, the library is enriched with the tooth models resulting from the implementation of the method described in WO 2016 066651 or of the step A) or A') described above.

One or several tooth attributes, in particular chosen from the list supplied above, are associated with the tooth models. A tooth attribute value is assigned to each tooth attribute of a particular tooth model, as described previously (see the description of the step A)). For example, a tooth model is that of an "incisor", "greatly worn", and whose color parameters are, in the color system L*a*b* according to the standard NF ISO 7724, "a*=2", "b*=1" and "L*=58".

Figure 18:
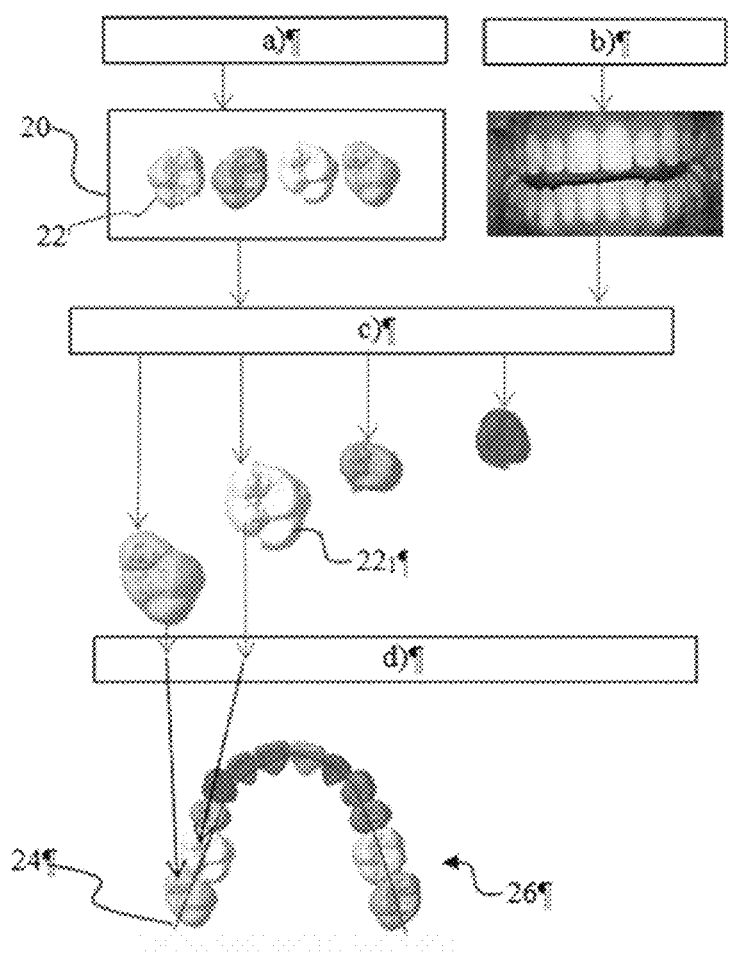

The historical library therefore contains historical tooth models and associated attribute values which facilitate the search in the step c). In FIG. 18, only historical tooth models 22 representing molars have been represented in the historical library 20.

In the step b), an analysis image is acquired, as described above for the step B), before analyzing it. In particular, the analysis image is preferably a photo or an image from a film, preferably with a cellphone.

The analysis image can be acquired at any moment after the step a), for example more than one week, more than one month or more than six months after the step a).

The analysis image is analyzed according to a detailed analysis method according to the invention. The optional features of this method are also optional in the step b).

On completion of the step b), an analysis image is obtained that is enriched with a description providing, for each analysis tooth zone, a tooth attribute value for at least one tooth attribute, for example a tooth number.

In the step c), a search is carried out in the historical library, for each analysis tooth zone determined in the preceding step, for a historical tooth model exhibiting a maximal proximity with the analysis tooth zone. This tooth model is qualified as "optimal tooth model".

The "proximity" is a measurement of one or more differences between the historical tooth model and the analysis tooth zone. These differences may include a difference in shape, but also other differences like a difference in translucency or in color. The maximal proximity may be searched for by successively minimizing several differences, or by minimizing a combination of these differences, for example a weighted sum of these differences.

The "proximity" is therefore a broader concept than "match", the match measuring only a shape-related proximity.

The assessment of the proximity of a historical tooth model with an analysis tooth zone preferably comprises a comparison of at least one value of a tooth attribute of the analysis tooth zone with the value of this attribute for the historical tooth model. Such an assessment is advantageously very rapid.

For example, if the description of the analysis tooth zone provides a value for the type or the number of the tooth, the thickness of the tooth represented and/or the height of its crown and/or its mesio palatine width and/or the mesial and distal deflection index of its incisal edge, this value may be compared to the value of the corresponding attribute of each of the historical tooth models.

Preferably, a historical tooth model is sought that has, for at least one tooth attribute, the same value as said analysis tooth zone. The tooth attribute may in particular relate to the tooth type or to the tooth number. In other words, the historical tooth models are filtered to examine in more detail only those which relate to the same type of tooth as the tooth represented on the analysis tooth zone.

Alternatively or, preferably, in addition to this comparison of the attribute values, the shape of the tooth represented on the analysis tooth zone may be compared to the shape of a historical tooth model to be assessed, preferably by means of a metaheuristic method, preferably evolutionist, preferably by simulated annealing.

To this end, the historical tooth model to be assessed is observed from different angles. Each view thus obtained is compared with the analysis image, preferably with the analysis tooth zone, so as to establish a "distance" between this view and said analysis image or, preferably, said analysis tooth zone. The distance thus measures the difference between the view and the analysis tooth zone.

The distance may be determined after a processing of the view and of the analysis image or, preferably, of the analysis tooth zone, so as to reveal, on corresponding maps, one and the same discriminating information item, for example a contour information item, as described above in the step C3) or in WO 2016 066651.

For each historical tooth model tested, a view is thus determined which provides a minimal distance with the analysis image or with the analysis tooth zone. Each historical tooth model examined is thus associated with a particular minimal distance, which measures its proximity of shape with the analysis tooth zone.

The optimal historical tooth model is the one which, in light of the comparison or comparisons performed, is considered to be closest to the analysis tooth zone.

The minimal distances obtained for the different tooth models tested are then compared and, to define the optimal tooth model, the one which exhibits the smallest minimal distance is retained. The optimal tooth model therefore exhibits a maximal match with the analysis image.

The search for the maximal match is preferably performed by means of a metaheuristic method, preferably evolutionist, preferably by simulated annealing.

In a preferred embodiment, a first assessment of the historical tooth models by comparison of the values of at least one tooth attribute, for example the tooth number, with the corresponding values of the analysis tooth zone, then a second assessment by comparison of shape are performed in succession. The first, rapid assessment, advantageously makes it possible to filter the historical tooth models in order to submit only the historical tooth models retained by the first assessment to the second, slower assessment.

For example, if an analysis tooth zone represents a tooth number 15, the first assessment makes it possible to retain only the tooth models modeling teeth number 15. During the second assessment, a search is conducted, among all the historical tooth models modeling teeth number 15, for the historical tooth model whose shape most approximates that of the tooth represented.

More preferably, several first assessments are performed before performing the second assessment. For example, the first assessments make it possible to filter the historical tooth models so as to retain only the tooth models modeling teeth number 15 and which exhibit a crown height of between 8 and 8.5 mm.

On completion of the step c), an optimal tooth model has thus been associated with each of the analysis tooth zones.

For example, in FIG. 18, the historical tooth model $22_1$ can be observed so as to strongly resemble an analysis zone identified on the analysis image. It is considered as optimal for this analysis zone.

In the step d), an assembled model is created by arranging the optimal tooth models.

According to one embodiment, at the start of the step d), a first rough arrangement is created, that is to say that a rough model is produced by assembling optimal tooth models.

To establish the first rough arrangement, the optimal tooth models can be oriented so that their optimal directions of observation are all parallel, the optimal direction of observation of a tooth model being the direction in which said tooth model exhibits a maximum match with the analysis image.

The first rough arrangement may be also established by considering the tooth attribute values of the optimal tooth models. For example, if the tooth numbers of optimal tooth models are those of the canines and of the incisors, these tooth models may be arranged according to an arc 24 (FIG. 18) corresponding conventionally to the region of the arch which bears these types of teeth.

The shape of this arc may be refined as a function of other tooth attribute values.

The order of the optimal tooth models is that of the corresponding analysis tooth zones.

Moreover, the minimal distance associated with an optimal tooth model results from an observation of the tooth model according to an "optimal" observation direction. In other words, it is probably substantially from this direction that the tooth that this model models is also observed in the analysis image. All the optimal tooth models are thus preferably oriented in such a way that their respective optimal observation directions are all parallel.

It is thus possible to define a first arrangement of the optimal tooth models.

Preferably, the first arrangement of the optimal tooth models is then modified iteratively, so as to exhibit a maximal match with the analysis image.

To assess an arrangement, it is observed according to different angles. Each view thus obtained is compared with the analysis image so as to establish a "distance" between this view and said analysis image. The distance thus measures the difference between the view and the analysis image.

The distance may be determined after a processing of the view and of the analysis image so as to reveal, on one of the corresponding maps, a discriminating information item, for example a contour information item, as described above in the step C3) or in WO 2016 066651.

For each arrangement examined, a view is thus determined that provides a minimal distance with the analysis image. Each arrangement examined is thus associated with a minimal distance.

The minimal distances obtained for the different arrangements tested are then compared and, to define the optimal arrangement, the one which exhibits the smallest minimal distance is retained. The optimal arrangement thus exhibits a maximal match with the analysis image.

The search for the maximal match is performed preferably by means of a metaheuristic method, preferably evolutionist, preferably by simulated annealing.

On completion of the step d), an optimal arrangement of the optimal tooth models, that is to say the assembled model 26, is obtained.

In the optional step e), one or more optimal tooth models are replaced by other tooth models, then there is a return to the step d) so as to maximize the match between the assembled model and the analysis image.

It is in fact possible for an optimal tooth model, in the "optimal" arrangement, to no longer exhibit a maximal match with the analysis image. In particular, the tooth model might have been observed in an "optimal" direction which provided a view exhibiting a minimal distance with the analysis image (reason why it was considered as optimal), but, in the optimal arrangement, it is no longer oriented according to the optimal direction.

A new search for an assembled model may therefore be performed by modifying the tooth models, for example by replacing the optimal tooth models with close tooth models.

The search for the tooth models to be tested is preferably performed by means of a metaheuristic method, preferably evolutionist, preferably by simulated annealing.

In the preferred embodiment, the method therefore implements a double optimization, on the tooth models and on the arrangement of the tooth models, the assembled model being the arrangement of a set of tooth models which provides the minimal distance with the analysis image, by considering all the possible tooth models and all the possible arrangements.

In the optional and preferred step f), the method implements several analysis images of the arch of the patient, preferably more than 3, more than 5, more than 10, more than 50, preferably more than 100 analysis images. The assembled model is thus more complete. More preferably, the method implements an optimization such that the assembled model obtained is optimal in light of all of the analysis images. In other words, the assembled model is preferably the one which maximizes the match with all of the analysis images.

In the preferred embodiment, the method therefore implements a double or, preferably a triple optimization, on the tooth models on the one hand, on the arrangement of the tooth models and/or on a plurality of analysis images on the other hand, the assembled model being the arrangement of a set of tooth models which provides the mean minimal distance, over all of the analysis images, by considering all the possible tooth models and, preferably, all the possible arrangements.

According to one embodiment, in the step d) and/or e) and/or f), a metaheuristic, preferably evolutionist, method, preferably by simulated annealing, is used.

As now clearly appears, the invention thus makes it possible to construct an assembled dental arch model from simple analysis images, for example photographs taken by means of a cellphone. Obviously, the accuracy of the assembled model does not reach that of a scan. In some applications, for example to perform a first diagnosis of the dental situation of the patient, such an accuracy is not however essential.

The assembled model may therefore be used to analyze the orthodontic situation of the patient, according to the steps ii) to iv).

In the step ii), the assembled model is sent to an orthodontist and/or to a computer provided with diagnostic software.

In one embodiment, the assembled model is sent accompanied by a questionnaire filled out by the patient in order to improve the quality of the analysis in the step iv).

In the step iii), the orthodontist and/or the computer examines the assembled model. Unlike an updated image, the assembled model allows an observation from any angle. The analysis is advantageously more accurate.

In the step iv), the orthodontist and/or the computer informs the patient, for example by sending him or her a message on his or her telephone. This message may in particular inform the patient of an unfavorable situation and urge him or her to make an appointment with the orthodontist.

The orthodontist may also compare the assembled model with assembled models received previously for the same patient. The analysis thereof advantageously makes it possible to assess the trend of the situation. The message may thus inform the patient of an unfavorable change of his or her situation, which improves the prevention.

The assembled model may also be compared with one or more models obtained by scanning of the teeth or from a molding of the teeth of the patient, or with an updated reference model resulting from the implementation of a method described in WO 2016 066651.

Application to Embedded Monitoring

An image analysis according to the invention is also useful for guiding the acquisition of an image of a dental arch, in particular for establishing a remote diagnosis.

In particular, WO 2016/066651 describes a method in which an initial reference model is deformed so as to obtain an updated reference model allowing the acquisition of reference images exhibiting a maximal match with the "updated" images of the arch acquired at the updated instant.

The reference images are therefore views of the updated reference model, observed in virtual acquisition conditions which are the closest possible matches with the real acquisition conditions implemented to acquire the updated images of the arch of the patient.

The search for these virtual acquisition conditions is preferably performed by means of metaheuristic methods.

To speed up this search, WO 2016/066651 recommends performing a first rough assessment of the real acquisition conditions. For example, conditions which would correspond to a position of the acquisition apparatus at a distance from the teeth greater than 1 meter are excluded from the search.

There is however an ongoing need to speed up the execution of the method described in WO 2016/066651, and in particular, to search, more rapidly, for the virtual acquisition conditions exhibiting a maximal match with the real acquisition conditions implemented to acquire an updated image of the arch of the patient.

One aim of the invention is to at least partially address this problem.

The invention proposes a method for acquiring an image of a dental arch of a patient, said method comprising the following steps:

a') activation of an image acquisition apparatus so as to acquire an image, called "analysis image", of said arch;

b') analysis of the analysis image by means of a deep learning device, preferably a neural network, trained by means of a learning base, preferably according to a detailed analysis method according to the invention, so as to identify at least one analysis tooth zone representing a tooth on said analysis image, and to determine at least one tooth attribute value for said analysis tooth zone, or according to a global analysis method according to the invention;

c') determination, for the analysis image, of a value for an image attribute, said value being a function of said tooth attribute value if a detailed analysis method according to the invention has been implemented in the preceding step;

d') optionally, comparison of said image attribute value with an instruction;

e') sending of an information message as a function of said comparison.

In one embodiment, in the step b'), all said analysis tooth zones are identified, and at least one tooth attribute value is determined for each analysis tooth zone, and, in the step c'), the value for the image attribute is determined as a function of said tooth attribute values.

In one embodiment, the step b') comprises the following steps:

1) preferably before the step a'), creation of a learning base comprising more than 1 000 dental arch images, or "historical images", each historical image comprising one or more zones each representing a tooth, or "historical tooth zones", to each of which, for said tooth attribute, a tooth attribute value is assigned;

2) training of at least one deep learning device, preferably a neural network, by means of the learning base;

3) submission of the analysis image to the deep learning device so that it determines at least one probability relating to:

the presence, at a location in said analysis image, of a zone representing, at least partially, a tooth, or "analysis tooth zone", the attribute value of the tooth represented on said analysis tooth zone, 4) determination, as a function of said probability, of the presence of a tooth at a position represented by said analysis tooth zone, and of the attribute value of said tooth.

In one embodiment, the step b') comprises the following steps:

1') creation of a learning base comprising more than 1 000 dental arch images, or "historical images", each historical image comprising an attribute value for at least one image attribute, or "image attribute value";

2') training of at least one deep learning device, preferably a neural network, by means of the learning base;

3') submission of the analysis image to the deep learning device so that it determines, for said analysis image, at least one probability relating to said image attribute value.

In one embodiment, to create a historical image of the learning base, an operator, preferably an orthodontist, identifies one more "historical" tooth zones on an image, then assigns each identified historical tooth zone a value for at least one tooth attribute, and/or assigns an image a value for at least one tooth attribute.

In one embodiment, the information message is sent by the acquisition apparatus.

As will be seen in more detail hereinafter in the description, an acquisition method according to the invention therefore makes it possible to check whether an analysis image respects an instruction and, if it does not respect the instruction, to guide the operator in order for him or her to acquire a new analysis image. The method therefore allows an "embedded monitoring", preferably in the image acquisition apparatus.

In particular, to implement the method of WO 2016/066651, there may be a desire to acquire updated images from different acquisition directions, for example a front image, a right image and a left image. These updated images, acquired in succession, may be classified accordingly. The search for the virtual acquisition conditions exhibiting a maximal match with the real acquisition conditions is speeded up thereby.

In effect, the search may begin from virtual acquisition conditions in which the virtual acquisition apparatus is in front, to the left or to the right of the updated reference model, depending on whether the updated image considered is classified as a front, left or right image, respectively.

The operator, generally the patient, may however make a mistake in the acquisition of the updated images. In particular, he or she may forget to take an updated image, for example the front view, or invert two updated images. Typically, the operator may take an image on the right whereas a left image is expected from him or her.

This inversion of the updated images may considerably slow down their processing. For example, if the updated image is assumed to be an image taken on the left but it was in error taken on the right, said search for the optimal virtual acquisition conditions, that is to say those exhibiting a maximal match with the real acquisition conditions, will begin from a starting point offering a left view of the reference model, whereas the optimal virtual acquisition conditions correspond to a right view. The search will therefore be considerably slowed down thereby.

By virtue of the invention, each updated image is an analysis image which may be analyzed and checked, preferably in real time.

For example, the acquisition method makes it possible to determine that the updated image has been "taken on the right" and compare this image attribute value with the instruction which had been given to the operator to take the updated image on the left. Since the attribute value of the updated image (image taken on the right) does not correspond to the instruction (acquire an updated image on the left), the acquisition apparatus may immediately alert the operator in order for him or her to modify the acquisition direction.

An acquisition method is now described in detail.

In the step a'), the operator activates the image acquisition apparatus so as to acquire an analysis image.

In one embodiment, the operator triggers the acquisition apparatus so as to store the analysis image, preferably takes a photo or video of his or her teeth, preferably by means of a cellphone equipped with a camera.

The step a') may be performed like the acquisition of the updated images in the step B) described above.

In another embodiment, the analysis image is not stored. In particular, the analysis image may be the image which, in real time, appears on the screen of the cellphone of the operator, generally the patient.

In a first embodiment, in the step b'), the analysis image is analyzed according to a detailed analysis method according to the invention. This analysis preferably leads to the assignment of a tooth attribute value to each identified analysis tooth zone, for example to assigning a tooth number to each of the analysis tooth zones.

In the step c'), an attribute value of the analysis image is determined as a function of the tooth attribute values. The attribute value of the analysis image may relate to its general orientation and may for example take one of the following three values: "right photo", "left photo" and "front photo". The attribute value of the analysis image may also be the list of the tooth numbers represented, for example, "16, 17 and 18". The attribute value of the analysis image may also be, for example, the "presence" or "absence" of a dental, preferably orthodontic, appliance, or the state of opening of the mouth ("mouth open", "mouth closed").

In another embodiment, a global analysis method according to the invention is implemented in the step b'). Advantageously, such a method makes it possible to directly obtain a value for an image attribute, without having to determine values for a tooth attribute. It is therefore advantageously more rapid. The information resulting from a global analysis may however be less accurate than that resulting from a detailed analysis.

The steps a') to c') thus make it possible to characterize the analysis image.

The characterization of the analysis image makes it possible to guide the operator if the analysis image does not correspond to the expected image, for example because its quality is insufficient or because it does not represent the desired teeth.

In the step d'), the image attribute value of the analysis image is compared with an instruction.

For example, if the instruction was to acquire a right image and the image attribute value is "take on the left", the comparison leads to the conclusion that the image acquired is "unsatisfactory".

In the step e'), a message is sent to the operator, preferably by the acquisition apparatus.

Preferably, the information message relates to the quality of the image acquired and/or to the position of the acquisition apparatus in relation to said arch and/or to the setting of the acquisition apparatus and/or to the opening of the mouth and/or to the wearing of a dental, preferably orthodontic, appliance.

For example, if the image acquired is "unsatisfactory", the acquisition apparatus may emit a light, for example red, and/or ring, and/or generate a voice message, and/or vibrate, and/or display a message on its screen.

For example, if the image has to be acquired while the patient wears his or her dental appliance and this is not the case, the acquisition apparatus may send the message "wear your appliance for this image".

For example, if the image was acquired with the patient not sufficiently opening the mouth or with the mouth closed, the acquisition apparatus may send the message "open your mouth more for this image".

In one embodiment, the steps b') to c') are implemented only if the operator records the analysis image, that is to say he or she presses on the trigger. The message then prompts the operator to acquire a new analysis image. Optionally, the acquisition apparatus deletes the unsatisfactory analysis image.

In one embodiment, the steps b') to c') are implemented permanently when the acquisition apparatus is switched on and the analysis image is an image which appears on a screen of the acquisition apparatus. The acquisition apparatus may thus, for example, emit a red light as long as the analysis image is unsatisfactory, and emit a green light when the analysis image is satisfactory. Advantageously, the acquisition apparatus then stores only analysis images which are satisfactory.

As now clearly emerges, the invention therefore allows an embedded monitoring upon the acquisition of analysis images. When applied to updated images of the method of WO 2016/066651, the steps a') to e') make it possible to check that these images do indeed conform to the need, and therefore to considerably speed up the execution of this method.

The steps d') and e') are optional. In one embodiment, the analysis image is only associated with its description, which specifies its image attribute value. This description also makes it possible to considerably speed up the execution of the method of WO 2016/066651 since, when the analysis image is used as updated image of this method, it makes it possible to approximately determine the real acquisition conditions of this image, by eliminating the risk of a rough error, for example because of a reversal between two images.

The steps d') and e') are however preferred. They make it possible for example to avoid having the operator forget a left image, or take two redundant right images.

Application to the Monitoring of an Orthodontic Aligner

Conventionally, at the start of an orthodontic treatment, the orthodontist determines the positioning of the teeth that he or she wants to obtain at a so-called "set-up" instant of the treatment. The set-up may be defined by means of an imprint or from a three-dimensional scan of the teeth of the patient. The orthodontist then has manufactured, or manufactures, accordingly, an orthodontic appliance suited to this treatment.

The orthodontic appliance may be an orthodontic aligner. An aligner conventionally takes the form of a removable single-piece appliance, conventionally made of a transparent polymer material, which comprises a channel conformed for several teeth of an arch, generally all the teeth of an arch, to be able to be housed therein.

Figure 14:
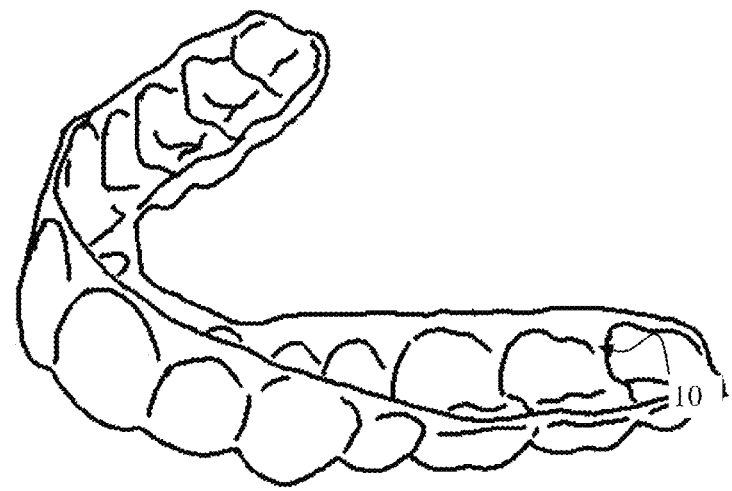
FIGS. 14 and 15 represent an orthodontic aligner, in perspective and plan views, respectively.
Figure 15:
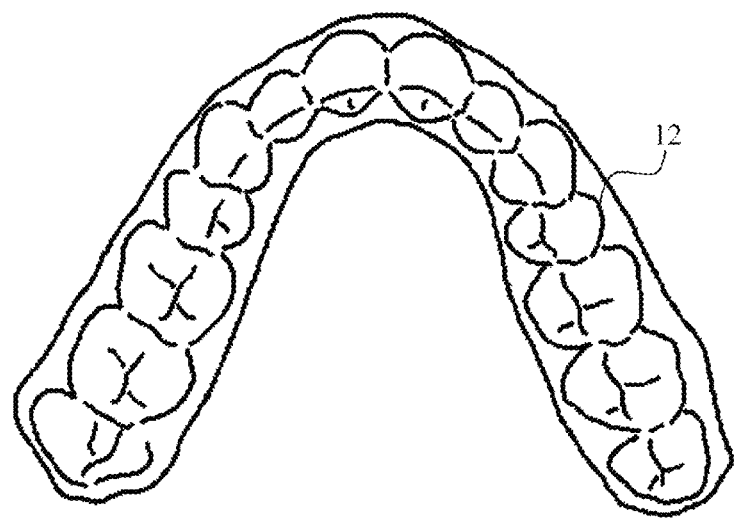

The form of the channel is adapted to hold the aligner in position on the teeth, while exerting an action of correction of the positioning of certain teeth (FIGS. 14 and 15).

At the start of the treatment, the shapes that the different aligners have to take at different moments of the treatment are conventionally determined, then the set of corresponding aligners is manufactured. At predetermined instants, the patient changes the aligner.

Figure 20:
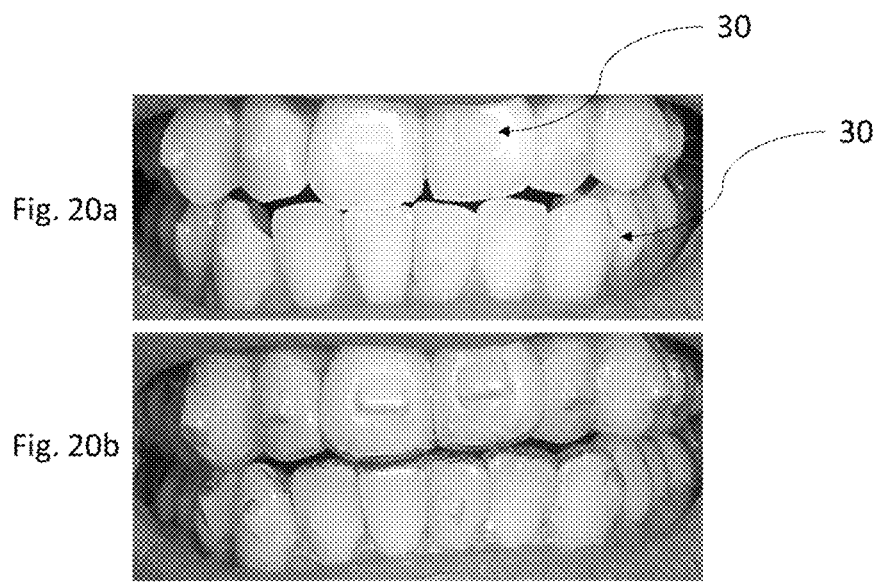
Figure 21:
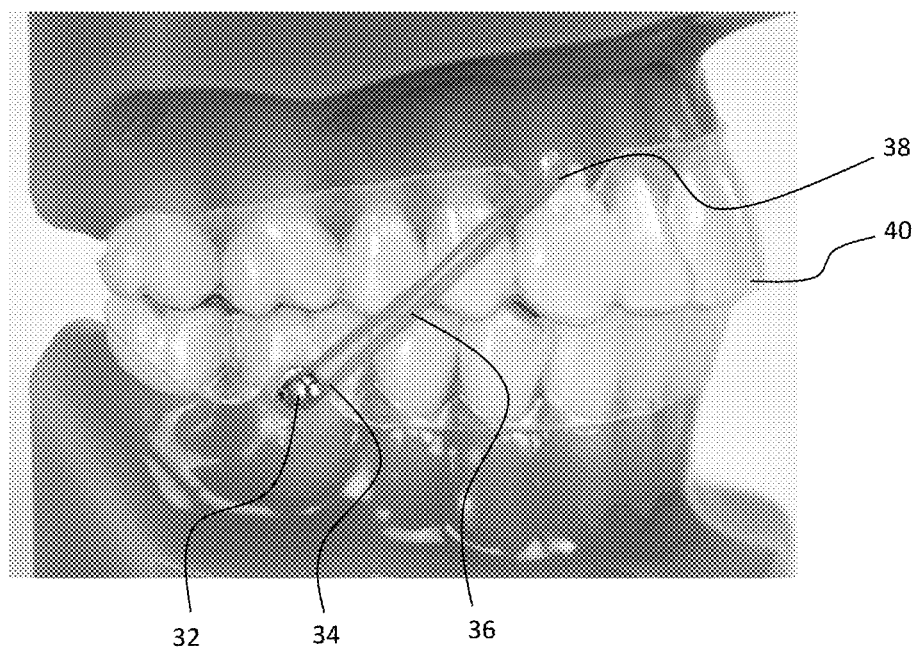
FIG. 21 illustrates a button fixed on a tooth of a patient.

At the start of the treatment, or during the treatment, the orthodontist may fix one or more attachments 30 (FIGS. 19 and 20) or buttons 32 (FIG. 21) on the teeth of the patient. An attachment facilitates, in particular, the movement of the tooth on which it is fixed on by allowing the orthodontic aligner to exert a greater action of correction of the positioning of the tooth on which the attachment is fixed on. As illustrated in FIG. 21, a button 32 is an anchoring element, usually made in a metal, which may be rigidly fixed on a tooth or on an orthodontic aligner, to attach a first end 34 of an elastic band 36. Another end 38 of the elastic band is attached on the orthodontic aligner 40, so that the elastic band exerts an action on said orthodontic aligner.

The treatment by means of aligners is advantageously less stressful for the patient. In particular, the number of appointments with the orthodontist is limited. Furthermore, there is less pain than with a metal orthodontic brace attached to the teeth.

The market for orthodontic aligners is therefore on the increase.

At regular intervals, the patient goes to the orthodontist for a visual inspection, notably to check whether the displacement of the teeth conforms to the expectations and whether the aligner worn by the patient is still suited to the treatment.

The orthodontist may also check if an attachment or a button has come off a tooth.

If the orthodontist diagnoses an unsuitability to the treatment, he or she takes a new imprint of the teeth, or, in an equivalent manner, a new three-dimensional scan of the teeth, then orders a new series of aligners configured accordingly. It is considered that, on average, the number of aligners finally manufactured is approximately 45, instead of 20 aligners conventionally provided at the start of the treatment.

The need to have to go to the orthodontist is a constraint for the patient. The trust of the patient in his or her orthodontist may also be affected. The inadequacy may be unsightly. Finally, the result thereof is an additional cost.

The number of inspection visits to the orthodontist must therefore be limited.

There is a need for solutions addressing these problems.

One aim of the invention is to at least partially address this need.

The invention provides a method for assessing the shape of an orthodontic aligner, said method comprising the following steps:
  a") acquisition of at least one image at least partially representing the aligner in a service position in which it is worn by a patient, called "analysis image";
  b") analysis of the analysis image by means of a deep learning device, preferably a neural network, trained by means of a learning base, so as to determine a value for at least one tooth attribute of an "analysis tooth zone" of the analysis image, the tooth attribute relating to a separation between the tooth represented by the analysis tooth zone, and the aligner represented on the analysis image, and/or
    for an image attribute of the analysis image, the image attribute relating to a separation between at least one tooth represented on the analysis image, and the aligner represented on said analysis image;
  c") preferably, assessment of the suitability of the aligner as a function of the value of said tooth or image attribute;
  d") preferably, sending of an information message as a function of said assessment.

As will be seen in more detail hereinafter in the description, an assessment method according to the invention considerably simplifies the assessment of the good suitability of the aligner to the treatment, while making this assessment particularly reliable. In particular, the method may be implemented from simple photographs or films, taken with no particular precautions, for example by the patient. The number of appointments with the orthodontist may therefore be limited.

Preferably, in the step b"), all said analysis tooth zones are identified, and the value of said tooth attribute is determined for each analysis tooth zone, and, in the step c"), the suitability of the aligner is determined as a function of said tooth attribute values.

Preferably, said tooth attribute is chosen from the group formed by a maximal separation along the free edge of the tooth, a mean separation along the free edge of the tooth, and said image attribute is chosen from the group formed by a maximal separation along all of the teeth represented, a mean separation along the free edges of all of the teeth represented, an overall acceptability of the separation of the teeth represented.

The tooth attribute relating to a separation may in particular be the existence of a separation, this attribute being able to take the tooth attribute values "yes" or "no"; or a value measuring the scale of the separation, for example an observed maximal separation or an assessment in relation to a scale.

Alternatively, or additionally, the tooth attribute allows to determine the loss of an attachment or of a button. Indeed, the existence of a separation may be due to the absence of an attachment or a button. In particular, the tooth attribute may qualify whether the separation relates to the absence of an attachment or of a button, or not.

The existence of a separation due to the absence of an attachment or of a button may be determined from the difference between the shape of the aligner relative to the shape of the tooth, and in particular, for an attachment, with the shape of the extrados surface of the tooth. In particular, the loss of an attachment creates a specific separation between this extrados surface and the surface of the aligner facing this extrados surface.

In the step b"), a detailed analysis method according to the invention is preferably implemented, a tooth attribute of each historical tooth zone of each historical image of the learning base relating to a separation between the tooth represented by the historical tooth zone, and an aligner worn by said tooth and represented on said historical image.

Preferably, the step b") comprises the following steps:
b"1) preferably before the step a"), creation of a learning base comprising more than 1000, preferably more than 5000, preferably more than 10 000 images of dental arches, or "historical images", each historical image representing an aligner worn by a "historical" patient and comprising one or more zones each representing a tooth, or "historical tooth zones", to each of which is assigned, for at least one tooth attribute relating to a separation between the tooth represented by the historical tooth zone considered, and the aligner represented, a tooth attribute value;
b"2) learning of a deep learning device, preferably a neural network, by means of the learning base;
b"3) submission of the analysis image to the deep learning device for the deep learning device to determine at least one probability relating to
the presence, at a location of said analysis image, of an analysis tooth zone, and
the tooth attribute value of the tooth represented on said analysis tooth zone;
b"4) determination, as a function of said probability, of the presence of a separation between the aligner and the tooth represented by said analysis tooth zone, and/or of an amplitude of said separation.

The steps b" 1) to b"4) may comprise one or more of the features, possibly optional, of the steps 1) to 4) described above, respectively.

In one embodiment, in the step b"), a global analysis method according to the invention is implemented, an image attribute of each historical image of the learning base relating to a separation between at least one tooth represented on the historical image, and an aligner worn by said tooth and represented on said historical image.

Preferably, the step b") comprises the following steps:
b"1') creation of a learning base comprising more than 1000 images of dental arches, or "historical images", each historical image comprising an attribute value for at least one image attribute, or "image attribute value", relating to a separation between at least one tooth represented on the analysis image, and the aligner represented on said analysis image;
b"2') training of at least one deep learning device, preferably a neural network, by means of the learning base;
b"3') submission of the analysis image to the deep learning device for it to determine, for said analysis image, at least one probability relating to said image attribute value, and determination, as a function of said probability, of the presence of a separation between the aligner and the tooth or teeth represented on the analysis image, and/or of an amplitude of said separation.

The steps b"1') to b"3') may comprise one or more of the features, possibly optional, of the steps 1') to 3') described above, respectively.

The method is now described when a detailed analysis is implemented in the step b").

Prior to the step a"), the learning base must be enriched, preferably according to an enrichment method according to the invention, in order to contain historical images whose description specifies, for each of the historical tooth zones, a value for the tooth attribute relating to the separation.

This information may be input manually. For example, an image representing one or more so-called "historical" tooth zones may be presented to an operator, preferably an orthodontist, and he or she may be asked to identify these historical tooth zones and indicate, for each historical tooth zone, whether there is a separation or not and/or assess the amplitude of this separation.

A historical image may be a photo representing an aligner worn by a historical patient. Alternatively, a historical image may be the result of a processing of an image representing a naked dental arch (that is to say without aligner) and of an image representing the same arch bearing the aligner. The image representing the naked arch may in particular be a view of a model of the arch deformed to obtain a maximal match with the image representing the arch bearing the aligner. Such a processing may in particular be useful for better revealing the outline of the teeth and of the aligner when the teeth are not very visible through the aligner.

Figure 19:
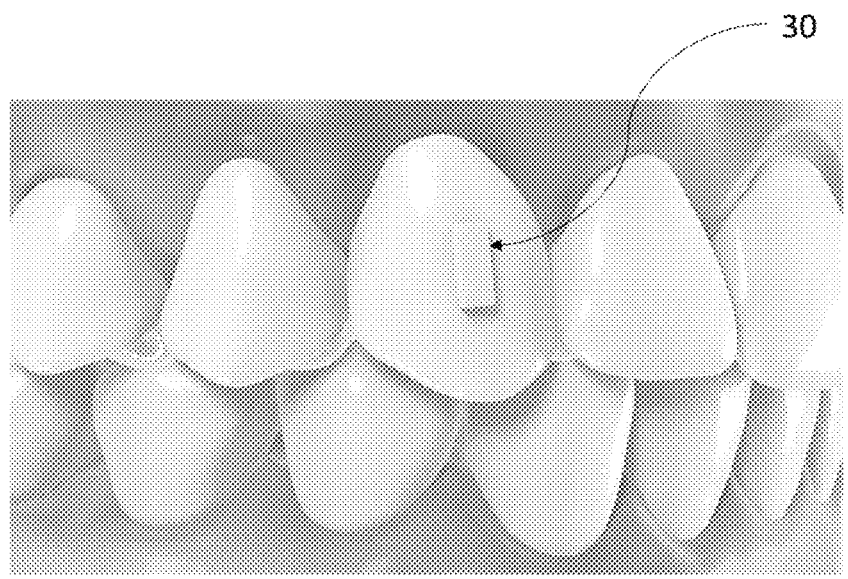
FIGS. 19 and 20 (20a and 20b) illustrate attachments fixed on the teeth of a patient.

An image representing a naked dental arch may include attachment as illustrated in FIG. 19, and FIG. 20a, and/or may include a button, as illustrated in FIG. 21. FIG. 20b illustrated the image representing the same dental arch of FIG. 20a bearing the aligner.

In the step a"), the acquisition of the analysis image may be performed like the acquisition of the updated images in the step B) described above.

Preferably, at least one reminder informing the patient of the need to create an analysis image is addressed to the patient. This reminder may be in paper form or, preferably, in electronic form, for example in the form of an email, of an automatic alert from a dedicated mobile device or an SMS. Such a reminder may be sent by the orthodontic practice or laboratory or by the dentist or by the dedicated mobile application of the patient, for example.

The step a") is performed at the moment when the assessment of the shape of an aligner is desired, for example more than 1 week after the start of the treatment with the aligner.

The analysis image is an image representing the aligner worn by the teeth of the patient.

In the step b"), the analysis image is analyzed according to a detailed analysis method according to the invention.

The deep learning device has been trained by means of a learning base containing historical images whose description specifies, for at least one, preferably each historical tooth zone, a value for a tooth attribute relating to a separation between the tooth represented by the historical tooth zone and the aligner worn by said tooth and represented on said historical image.

The value for this tooth attribute therefore provides an information item relating to the shape of the aligner relative to the shape of the teeth of the patient.

In one embodiment, the shape of the teeth of the patient includes the attachment(s) and/or the button(s) fixed on the tooth/teeth of the patient.

The value for this tooth attribute can be a measurement of the separation, for example a measurement of the maximum separation, or of the mean separation for the tooth represented by the historical tooth zone.

The deep learning device is therefore capable of analyzing the analysis image to determine, preferably for each of the "analysis tooth zones", the existence, even the extent, of a separation of the aligner of the tooth represented on the analysis tooth zone.

In the step c"), an assessment is made, as a function of the results of the preceding step, as to the compatibility of the aligner. For example, a search is conducted to see if the separation of the aligner with at least one tooth exceeds an acceptability threshold and, in this case, a decision is made as to the replacement of the aligner by a better suited aligner.

The suitability of the aligner can be assessed in the context of an orthodontic treatment (separation compatible or not with the orthodontic treatment) but also in the context of a non-therapeutic, in particular esthetic, treatment. Aligners can indeed be used to displace teeth for purely esthetic purposes, without this displacement modifying the state of health of the patient. The suitability of the aligner can also be assessed in the context of a research program concerning the effectiveness of the aligner, for example to assess a new material for the aligner, on a human being or on another animal.

The assessment of the suitability of the aligner may include the assessment of an absence of an attachment and/or of a button which should be fixed on a tooth of the patient. In particular, an attachment is supposed to be interposed between said tooth and said aligner in the service position.

An attachment, or a button, is rigidly fixed on a tooth and its external surface may be regarded as part of the surface defining the "shape of the tooth". The loss of an attachment or of a button therefore changes the "surface of the tooth", and will create a separation between the tooth and the aligner. This separation will therefore be induced by a change in the "shape of the tooth", and not by an unexpected movement of the tooth or to a wrong design of the aligner. The compatibility of the aligner may be assessed at step c") depending on this separation. A non compatibility will be associated with the loss of the attachment or of the button, and not necessarily associated to a wrong shape of the aligner. The information message at step d") will be adapted accordingly.

The loss of an attachment is an issue if said attachment was intended to act to move a tooth, in cooperation with the aligner worn by the patient at step a") and/or with future aligners to be worn after the aligner worn by the patient at step a"), said tooth being considered to be "active".

In a preferred embodiment, at step c"), the "activity" of the tooth on which the missing attachment should be rigidly fixed is assessed, preferably by a computer and/or by an orthodontist. The absence of an attachment and/or of a button fixed on a tooth of the patient is only regarded as an issue if the aligner is intended to act on said tooth.

Preferably, at step d"), the information message depends on said activity. Preferably, it informs about this activity of the tooth and/or is only emitted if said tooth is active, for instance for the patient to take an appointment with the orthodontist to replace the missing attachment.

In the step d"), an information item relating to the assessment in the preceding step is sent, in particular to the patient and/or the orthodontist.

The orthodontist can then use this information, possibly in combination with additional information, for example the age of the patient or the duration for which the aligner has been worn, to establish a diagnosis and, if necessary, decide on a suitable treatment.

In one embodiment, the method comprises, in the step b"), a global analysis according to the invention. The other steps are unchanged.

The analysis of the analysis image and of the historical images is then performed globally, without identification of the individual situation of each of the teeth represented and the image attribute relates to the image as a whole.

For example, the image attribute relating to the separation may relate to the acceptability of a dental situation, the cause of one or more separations, or relate to the global scale of the separation or separations of the teeth. For example, the value of the image attribute may be "globally acceptable" or "globally unacceptable". The value of the image attribute can also, for example, be a measurement of the separation, for example a measurement of the maximum separation, or of the mean separation between the teeth represented on the analysis image and the aligner.

As now clearly emerges, a method according to the invention makes it possible, from simple photos or a simple film, to determine whether the aligner is abnormally detached, even, if a detailed analysis was performed in the step b"), to determine the regions in which the aligner is separated from the teeth and assess the scale of this separation.

The invention also relates to a method for adapting an orthodontic treatment, a method in which a method for assessing the shape of an orthodontic aligner according to the invention is implemented, then, as a function of the result of said assessment, a new aligner is manufactured and/or the patient is counseled, for example for him or her to improve the conditions of use of his or her orthodontic aligner, in particular the positioning and/or the time bands when it should be worn and/or the maintenance of his or her orthodontic aligner, in order to optimize the treatment.

The use of aligners is not limited to therapeutic treatments. In particular, an assessment method may be implemented to assess an aligner exclusively used for esthetic purposes.

The method may also be used to assess other dental, in particular orthodontic, parts or appliances.

Computer Program

The invention relates also:
- to a computer program, and in particular a dedicated application for cellphones, comprising program code instructions for the execution of one or more steps of any method according to the invention, when said program is run by a computer,
- to a computer medium on which such a program is stored, for example a memory or a CD-ROM.

Obviously, the invention is not limited to the embodiments described above and represented.

In particular, the patient is not necessarily a human being. A method according to the invention may be used for another animal.

The patient could be alive or dead. He is preferably alive.

The methods of the invention may be used for an orthodontic treatment, but also out of any orthodontic treatment, and even out of any therapeutic treatment.

The invention claimed is:

1. A method of orthodontic treatment of a patient, the method comprising:
    receiving an assessment of the suitability of an aligner as a function of the value of:
        an image attribute of an analysis image, the image attribute relating to a separation between at least one tooth represented on the analysis image and the aligner represented on the analysis image,
        said analysis image being an image of an aligner in a service position in which it is worn by the patient acquired by a cellphone more than 1 week after the start of the treatment with the aligner, and being a photograph, or an image extracted from a film, wherein the image attribute was determined by an analysis of the analysis image that used a deep learning device trained by a learning base; and
    using the assessment to administer a suitable treatment, wherein the suitable treatment comprises maintenance of treatment with the aligner, an improvement in the conditions of use of the aligner, or replacement of the aligner with a better suited aligner,
    wherein the learning base comprised more than 1000 images of dental arches or "historical images",
        wherein each of the historical images represented an aligner worn by a "historical" patient and comprising one or more zones each representing a tooth or "historical tooth zones",
        wherein a historical tooth attribute value was assigned to each historical tooth zone, and
        wherein the historical tooth attribute value related to a separation between the historical tooth and the aligner represented on the historical image, and
        wherein the analysis image is submitted to the deep learning device for it to determine at least one probability relating to:
    the presence, in a location of said analysis image, of an analysis tooth zone; and
    the attribute value of the tooth represented on said analysis tooth zone;
    and wherein, as a function of said probability, at least one of
        the presence of a separation of the aligner and of the tooth represented by of said analysis tooth zone and an amplitude of the separation is determined.

2. The method of claim 1, wherein the conditions comprise the positioning or time bands when the aligner should be worn.

3. The method of claim 1, wherein the deep learning device is a neural network.

4. A system comprising:
    a non-transitory computer medium storing computer-program instructions for executing of one or more steps of a method of orthodontic treatment of a patient;
    wherein the method comprising:
        participating in communication, which includes sending and receiving, of an assessment of the suitability of an aligner as a function of the value of:
            an image attribute of an analysis image, the image attribute relating to a separation between a tooth represented on the analysis image and the aligner represented on the analysis image,
            said analysis image being an image of an aligner in a service position in which it is worn by the patient acquired by a cellphone more than 1 week after the start of the treatment with the aligner, and being a photograph, or an image extracted from a film,
            wherein the image attribute was determined by an analysis of the analysis image that used a deep learning device trained by a learning base,
        wherein the learning base comprises more than 1000 images of dental arches or "historical images",
            wherein each of the historical images represented an aligner worn by a "historical" patient and comprising one or more zones each representing a tooth or "historical tooth zones",
            wherein each historical zone represented a historical tooth,
            wherein a historical tooth attribute value was assigned to each historical zone, and
            wherein the historical tooth attribute value related to a separation between the historical tooth and the aligner represented on the historical image,
        and wherein:
            the analysis image is submitted to the deep learning device for it to determine at least one probability relating to:
                the presence, in a location of said analysis image, of an analysis tooth zone; and
                the attribute value of the tooth represented on said analysis tooth zone; and
                and wherein, as a function of said probability, at least one of the presence of a separation of the aligner and of the tooth represented by at least one of said analysis tooth zone and an amplitude of the separation is determined.

5. The system of claim 4, wherein the assessment is used to administer a suitable treatment, wherein the suitable treatment comprises maintenance of treatment with the aligner, an improvement in the conditions of use of the aligner, or replacement of the aligner with a better suited aligner.

6. The system of claim 5, wherein the conditions comprise the positioning or time bands when the aligner should be worn.

7. The system of claim 4, wherein the deep learning device is a neural network.

8. A method of orthodontic treatment of a patient, the method comprising:
    receiving an assessment of the suitability of an aligner as a function of the value of:
        an image attribute of an analysis image, the image attribute relating to a separation between at least one tooth represented on the analysis image and the aligner represented on the analysis image,
        said analysis image being an image of an aligner in a service position in which it is worn by the patient acquired by a cellphone more than 1 week after the start of the treatment with the aligner, and being a photograph, or an image extracted from a film, wherein the image attribute was determined by an analysis of the analysis image that used a deep learning device trained by a learning base; and
    using the assessment to administer a suitable treatment, wherein the suitable treatment comprises maintenance of treatment with the aligner, an improvement in the conditions of use of the aligner, or replacement of the aligner with a better suited aligner, wherein the learning base comprised more than 1000 images of dental arches or "historical images", wherein each of the historical images comprising an attribute value for at least one image attribute or "image attribute value", wherein the image attribute value related to a separation between the tooth or teeth and the aligner represented on the historical image, and wherein the analysis image is submitted to the deep learning device for it to determine at least one probability relating to said image attribute value.

9. The method of claim 8, wherein the conditions comprise the positioning or time bands when the aligner should be worn.

10. The method of claim 8, wherein the deep learning device is a neural network.

11. A system comprising:
    a non-transitory computer medium storing computer-program instructions for executing of one or more steps of a method of orthodontic treatment of a patient;
    wherein the method comprising:
    participating in communication, which includes sending and receiving, of an assessment of the suitability of an aligner as a function of the value of:
    an image attribute of an analysis image, the image attribute relating to a separation between a tooth represented on the analysis image and the aligner represented on the analysis image,
    said analysis image being an image of an aligner in a service position in which it is worn by the patient acquired by a cellphone more than 1 week after the start of the treatment with the aligner, and being a photograph, or an image extracted from a film,
    wherein the image attribute was determined by an analysis of the analysis image that used a deep learning device trained by a learning base, wherein the learning base comprised more than 1000 images of dental arches or "historical images", wherein each of the historical images comprising an attribute value for at least one image attribute or "image attribute value", wherein the image attribute value related to a separation between the tooth or teeth and the aligner represented on the historical image, and wherein the analysis image is submitted to the deep learning device for it to determine at least one probability relating to said image attribute value.

12. The system of claim 11, wherein the conditions comprise the positioning or time bands when the aligner should be worn.

13. The system of claim 11, wherein the deep learning device is a neural network.

14. The system of claim 11, wherein the assessment is used to administer a suitable treatment, wherein the suitable treatment comprises maintenance of treatment with the aligner, an improvement in the conditions of use of the aligner, or replacement of the aligner with a better suited aligner.

\* \* \* \* \*